(12) United States Patent
Conrad et al.

(10) Patent No.: US 10,485,458 B2
(45) Date of Patent: *Nov. 26, 2019

(54) PHYSIOLOGICAL MEASUREMENT USING WEARABLE DEVICE

(71) Applicant: Verily Life Sciences LLC, Mountain View, CA (US)

(72) Inventors: Andrew Conrad, Mountain View, CA (US); Eric Peeters, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 385 days.

This patent is subject to a terminal disclaimer.

(21) Appl. No.: 15/588,061

(22) Filed: May 5, 2017

(65) Prior Publication Data

US 2017/0238853 A1    Aug. 24, 2017

Related U.S. Application Data

(63) Continuation of application No. 13/924,296, filed on Jun. 21, 2013, now Pat. No. 9,662,050.

(51) Int. Cl.
*A61B 5/00* (2006.01)
*A61B 5/145* (2006.01)
(Continued)

(52) U.S. Cl.
CPC ........ *A61B 5/14503* (2013.01); *A61B 5/0022* (2013.01); *A61B 5/02055* (2013.01);
(Continued)

(58) Field of Classification Search
CPC combination set(s) only.
See application file for complete search history.

(56) References Cited

U.S. PATENT DOCUMENTS

| 6,454,707 B1 | 9/2002 | Casscells, III et al. |
| 6,707,360 B2 | 3/2004 | Underwood et al. |

(Continued)

OTHER PUBLICATIONS

Arruebo, Manuel, et al., "Antibody-Conjugated Nanoparticles for Biomedical Applications," Journal of Nanomaterials, 2009, pp. 1-24.

(Continued)

*Primary Examiner* — Joanne M Hoffman
(74) *Attorney, Agent, or Firm* — McDonnell Boehnen Hulbert & Berghoff LLP

(57) ABSTRACT

A method for real-time, high-density physiological data collection includes automatically measuring, by a wearable device, one or more physiological parameters during each of a plurality of measurement periods, and upon conclusion of a measurement period, for each of the plurality of measurement periods, automatically transmitting by the wearable device data representative of the physiological parameters measured during that measurement period, to a server, the server configured to develop a baseline profile based on the data transmitted by the wearable device for the plurality of measurement periods. The measurement periods may extend through a plurality of consecutive days, and each of the consecutive days may include multiple measurement periods. At least some of the physiological parameters are measured by non-invasively detecting one or more analytes in blood circulating in subsurface vasculature proximate to the wearable device.

20 Claims, 17 Drawing Sheets

(51) Int. Cl.

| | | |
|---|---|---|
| *A61B 5/05* | (2006.01) | |
| *A61B 5/055* | (2006.01) | |
| *A61B 5/1455* | (2006.01) | |
| *A61B 5/0205* | (2006.01) | |
| *G16H 40/63* | (2018.01) | |
| *A61B 5/11* | (2006.01) | |
| *A61B 5/1459* | (2006.01) | |
| *A61N 2/00* | (2006.01) | |
| *G06F 19/00* | (2018.01) | |

(52) U.S. Cl.
CPC .......... *A61B 5/055* (2013.01); *A61B 5/0515* (2013.01); *A61B 5/1112* (2013.01); *A61B 5/1455* (2013.01); *A61B 5/1459* (2013.01); *A61B 5/4848* (2013.01); *A61B 5/681* (2013.01); *A61B 5/742* (2013.01); *A61B 5/7405* (2013.01); *A61B 5/7455* (2013.01); *A61N 2/002* (2013.01); *G06F 19/00* (2013.01); *G06F 19/3456* (2013.01); *G16H 40/63* (2018.01)

(56) References Cited

U.S. PATENT DOCUMENTS

| | | | |
|---|---|---|---|
| 7,214,190 | B1 | 5/2007 | Wilson |
| 7,844,314 | B2 | 11/2010 | Al-Ali |
| 8,137,698 | B2 | 3/2012 | Peyman |
| 8,323,188 | B2 | 12/2012 | Tran |
| 8,481,082 | B2 | 7/2013 | Peyman |
| 8,668,935 | B2 | 3/2014 | Peyman |
| 8,709,488 | B2 | 4/2014 | Peyman |
| 8,795,251 | B2 | 8/2014 | Peyman |
| 8,801,690 | B2 | 8/2014 | Peyman |
| 8,808,268 | B2 | 8/2014 | Peyman |
| 8,932,636 | B2 | 1/2015 | Peyman |
| 9,017,729 | B2 | 4/2015 | Peyman |
| 9,662,050 | B2 | 5/2017 | Conrad et al. |
| 2003/0232370 | A1 | 12/2003 | Trifiro |
| 2004/0122297 | A1 | 6/2004 | Stahmann et al. |
| 2005/0054907 | A1 | 3/2005 | Page et al. |
| 2006/0165805 | A1 | 7/2006 | Steinhoff et al. |
| 2006/0205564 | A1 | 9/2006 | Peterson |
| 2006/0258920 | A1 | 11/2006 | Burd et al. |
| 2007/0027367 | A1 | 2/2007 | Oliver et al. |
| 2007/0073558 | A1 | 3/2007 | Hall et al. |
| 2007/0219419 | A1 | 9/2007 | KenKnight et al. |
| 2007/0231393 | A1 | 10/2007 | Ritter et al. |
| 2007/0255122 | A1 | 11/2007 | Vol et al. |
| 2008/0046286 | A1 | 2/2008 | Halsted |
| 2009/0018418 | A1 | 1/2009 | Markle et al. |
| 2009/0118605 | A1 | 5/2009 | Van Duyne et al. |
| 2010/0010571 | A1 | 1/2010 | Skelton et al. |
| 2010/0049010 | A1 | 2/2010 | Goldreich |
| 2010/0072994 | A1 | 3/2010 | Lee et al. |
| 2010/0076321 | A1 | 3/2010 | Zhang et al. |
| 2010/0222657 | A1 | 9/2010 | Ibey et al. |
| 2011/0028803 | A1 | 2/2011 | Ollmar |
| 2012/0232918 | A1 | 9/2012 | Mack et al. |
| 2013/0267791 | A1 | 10/2013 | Halperin et al. |
| 2013/0330116 | A1 | 12/2013 | Mello et al. |
| 2014/0200423 | A1 | 7/2014 | Eisen et al. |
| 2014/0379273 | A1 | 12/2014 | Petisce et al. |

OTHER PUBLICATIONS

Liu, Hao-Li, et al., "Magnetic Resonance Monitoring of Focused Ultrasound/Magnetic Nanoparticle Tergeting Delivery of Therapeutic Agents to the Brain," PNAS Early Edition, 2010, pp. 1-6.

Shao, Huilin, et al., "Magnetic Nanoparticles for Biomedical NMR-Based Diagnostics," Beilstein Journal of Nanotechnology, 2010, 1, pp. 142-154.

Search Report and Written Opinion for PCT/US2014/042986 dated Oct. 16, 2014.

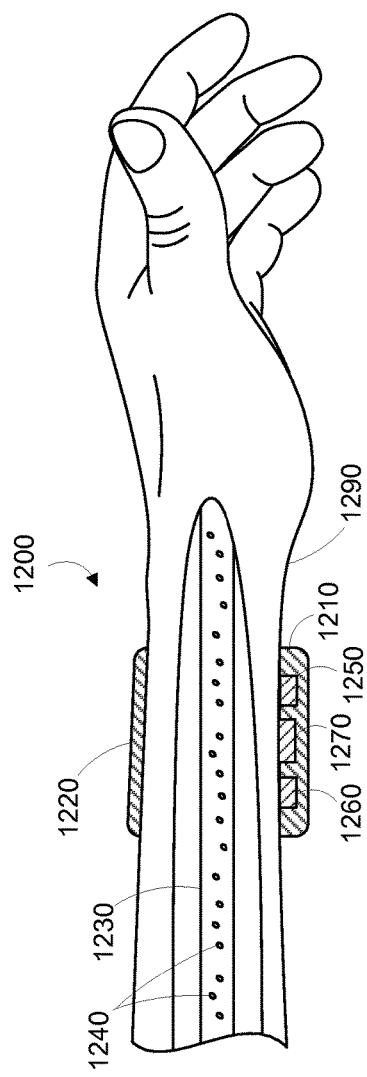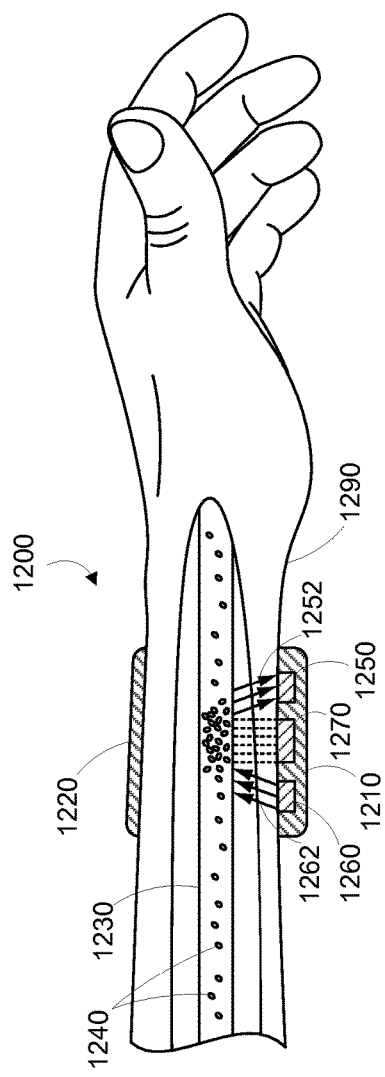

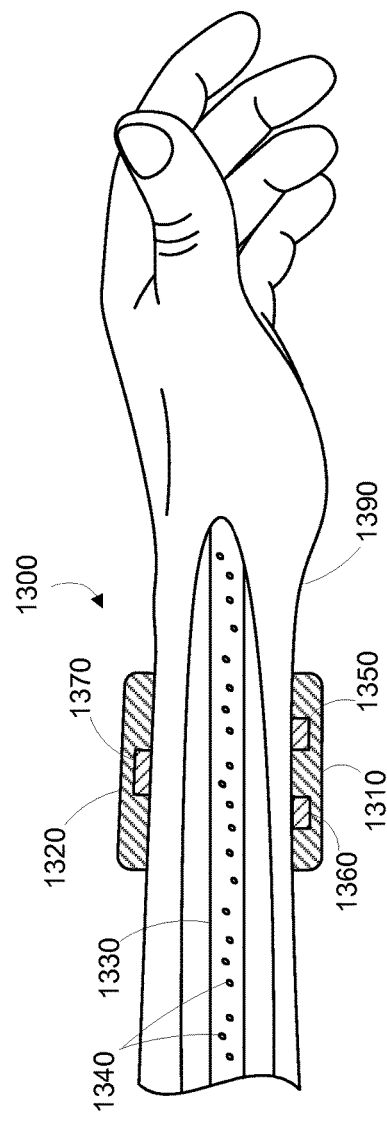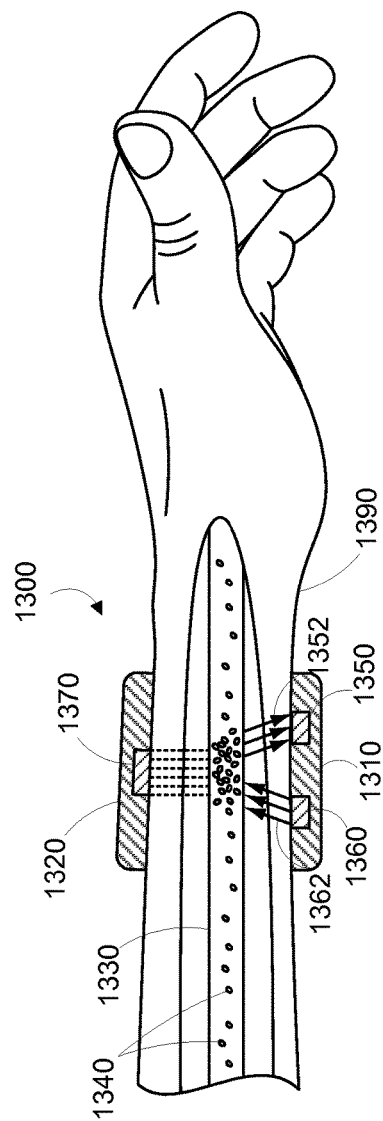

PHYSIOLOGICAL MEASUREMENT USING WEARABLE DEVICE

CROSS-REFERENCE TO RELATED APPLICATION

This application is a continuation of U.S. patent application Ser. No. 13/924,296, filed Jun. 21, 2013, which is incorporated herein by reference.

BACKGROUND

Unless otherwise indicated herein, the materials described in this section are not prior art to the claims in this application and are not admitted to be prior art by inclusion in this section.

A number of scientific methods have been developed in the medical field to measure physiological conditions of a person. For example, devices exist that may be used to measure physiological conditions such as a user's heart rate, blood pressure, skin temperature, breathing rate, etc.

Additional physiological parameters may be obtained by detecting and/or measuring one or more analytes in a person's blood. The one or more analytes could be any analytes that, when present in or absent from the blood, or present at a particular concentration or range of concentrations, may be indicative of a medical condition or health of the person. The one or more analytes could include enzymes, hormones, proteins, cells or other molecules.

In a typical scenario, a person's blood is drawn and sent to a lab where a variety of tests are performed to measure various analyte levels and parameters in the blood. The variety of tests may be referred to as "blood work," where the blood is tested for the presence of various diseases, or analyte levels such as cholesterol levels, etc. For most people, the blood tests are infrequent, and an abnormal analyte level indicative of a medical condition may not be identified until the next blood test is performed.

Even in the case of relatively frequent blood testing, such as may be found with those with diabetes, who regularly draw blood to test for blood glucose concentrations, those blood tests are typically performed when the user is awake, although the blood glucose levels (and potential variations in such levels) occurring during the night could provide important information to assist a physician in assessing that person's medical condition.

SUMMARY

Some embodiments of the present disclosure provide a method including: (i) automatically measuring, by a wearable device, one or more physiological parameters during each of a plurality of measurement periods and wherein at least one of the physiological parameters is measured by non-invasively detecting one or more analytes in blood circulating in subsurface vasculature proximate to the wearable device; and (ii) after conclusion of a measurement period for each of the plurality of measurement periods, developing a baseline profile based on the data transmitted by the wearable device for the plurality of measurement periods. The baseline profile may comprise an individual baseline profile based on the data measured by the wearable device for the plurality of measurement periods for an individual user wearing the wearable device.

In some examples, the wearable device is further configured to measure one or more physiological parameters during one or more additional measurement periods, detect a change in condition based on the individual baseline profile and the additional data, and generate one or more recommendations based on the detected change in condition and a clinical protocol. The wearable device may further comprise a user interface and the method may further comprise providing an indication of the one or more recommendations via the user interface. The wearable device may further be configured to receive, upon conclusion of a measurement period, an indication of the health state of a user of the wearable device for that measurement period; and derive a correlation between the health state of the user and the data representative of the physiological parameters measured during that measurement period.

Further embodiments provide introducing functionalized particles into a lumen of the subsurface vasculature, wherein the functionalized particles are configured to bind to the one or more analytes. The wearable device non-invasively may measure one or more analytes in blood circulating in subsurface vasculature proximate to the wearable device by: directing, from a signal source in the wearable device, an interrogating signal into the subsurface vasculature proximate to the wearable device; and detecting, by a detector in the wearable device, a response signal transmitted from the subsurface vasculature proximate to the wearable device in response to the interrogating signal, wherein the response signal is related to binding of the one or more analytes to the functionalized particles.

In some examples, the interrogating signal comprises a time-varying magnetic field and the response signal comprises an externally-detectable physical motion due of the functionalized particles to the time-varying magnetic field. In further examples, the interrogating signal comprises an electromagnetic pulse and the response signal comprises a magnetic resonance (MR) signal. The electromagnetic pulse may comprise a radio frequency (RF) pulse. In further examples, the interrogating signal comprises electromagnetic radiation having a wavelength between about 400 nanometers and about 1600 nanometers. The interrogating signal may comprise electromagnetic radiation having a wavelength between about 500 nanometers and about 1000 nanometers. In some examples, the particles may comprise a fluorophore, and the response signal may comprise fluorescence radiation transmitted by the fluorophore in response to the interrogating signal.

In further examples, the functionalized particles may be magnetic and the method further comprises: directing, from a magnet in the wearable device, a magnetic field into the subsurface vasculature proximate to the wearable device, wherein the magnetic field is sufficient to cause the functionalized magnetic particles to collect in a lumen of the subsurface vasculature proximate to the wearable device. The magnet may be configured to turn on the magnetic field and turn off the magnetic field.

Some embodiments of the present disclosure provide a method including: (i) automatically measuring, by a wearable device, one or more physiological parameters during each of a plurality of measurement periods and wherein at least one of the physiological parameters is measured by non-invasively detecting one or more analytes in blood circulating in subsurface vasculature proximate to the wearable device; and upon conclusion of a measurement period for each of the plurality of measurement periods, automatically transmitting by the wearable device data representative of the physiological parameters measured during that measurement period, to a server. The server may be configured to receive, upon conclusion of a measurement period, an indication of the health state of a user of the wearable device for that measurement period; and derive a correlation between the health state of the user and the data representative of the physiological parameters measured during that measurement period.

In further examples, the server may be configured to receive from the wearable device additional data representative of the physiological parameters measured during one or more additional measurement periods, detect a change in condition based on the baseline profile and the additional data, and generate one or more recommendations based on the detected change in condition and a clinical protocol, wherein the clinical protocol is developed based, at least in part, on the derived correlation.

In some examples, the server is further configured to receive data regarding physiological parameters measured by a plurality of wearable devices and receive an indication of the health state of the users of the plurality of wearable devices for a plurality of measurement periods; and derive a correlation between the health state of the users and the data representative of the physiological parameters measured during the plurality of measurement periods. The server may further be configured to receive from the wearable device additional data representative of the physiological parameters measured during one or more additional measurement periods and generate one or more recommendations based on the received additional data and a clinical protocol, wherein the clinical protocol is developed based, at least in part, on the derived correlation. In further examples, the server is further configured to: receive from the wearable device, an indication of the geographical location of the wearable device upon completion of a measurement period; and track geographical spreading of a disease based on the received geographical location and, at least in part, on the health state of the user and the measured physiological parameters. The server may further be configured to: receive information regarding one or more medications taken by the user; derive an indication of the effectiveness of the one or more medications taken by the user from, at least in part, the data representative of the physiological parameters measured during a measurement period and the health state of the user.

Some embodiments of the present disclosure provide a method including: (i) automatically measuring, by a wearable device, one or more physiological parameters during each of a plurality of measurement periods and wherein at least one of the physiological parameters is measured by non-invasively detecting one or more analytes in blood circulating in subsurface vasculature proximate to the wearable device; and after conclusion of a measurement period for each of the plurality of measurement periods, transmitting by the wearable device data representative of the physiological parameters measured during that measurement period, to a server, wherein the server is configured to develop a baseline profile based on the data transmitted by the wearable device for the plurality of measurement periods.

Some embodiments of the present disclosure provide non-transitory computer readable medium having stored therein instructions that are executable by a processor to cause a system to perform functions comprising: (i) automatically measuring, by a wearable device, one or more physiological parameters during each of a plurality of measurement periods, wherein at least one of the physiological parameters is measured by non-invasively detecting one or more analytes in blood circulating in subsurface vasculature proximate to the wearable device; and after conclusion of a measurement period, for each of the plurality of measurement periods, developing a baseline profile based on the data transmitted by the wearable device for the plurality of measurement periods.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 12A is side partial cross-sectional view of a wrist-mounted device, while on a human wrist.

FIG. 12B is side partial cross-sectional view of a wrist-mounted device, while on a human wrist.

FIG. 13A is side partial cross-sectional view of a wrist-mounted device, while on a human wrist.

FIG. 13B is side partial cross-sectional view of a wrist-mounted device, while on a human wrist.

DETAILED DESCRIPTION

Figure 1:
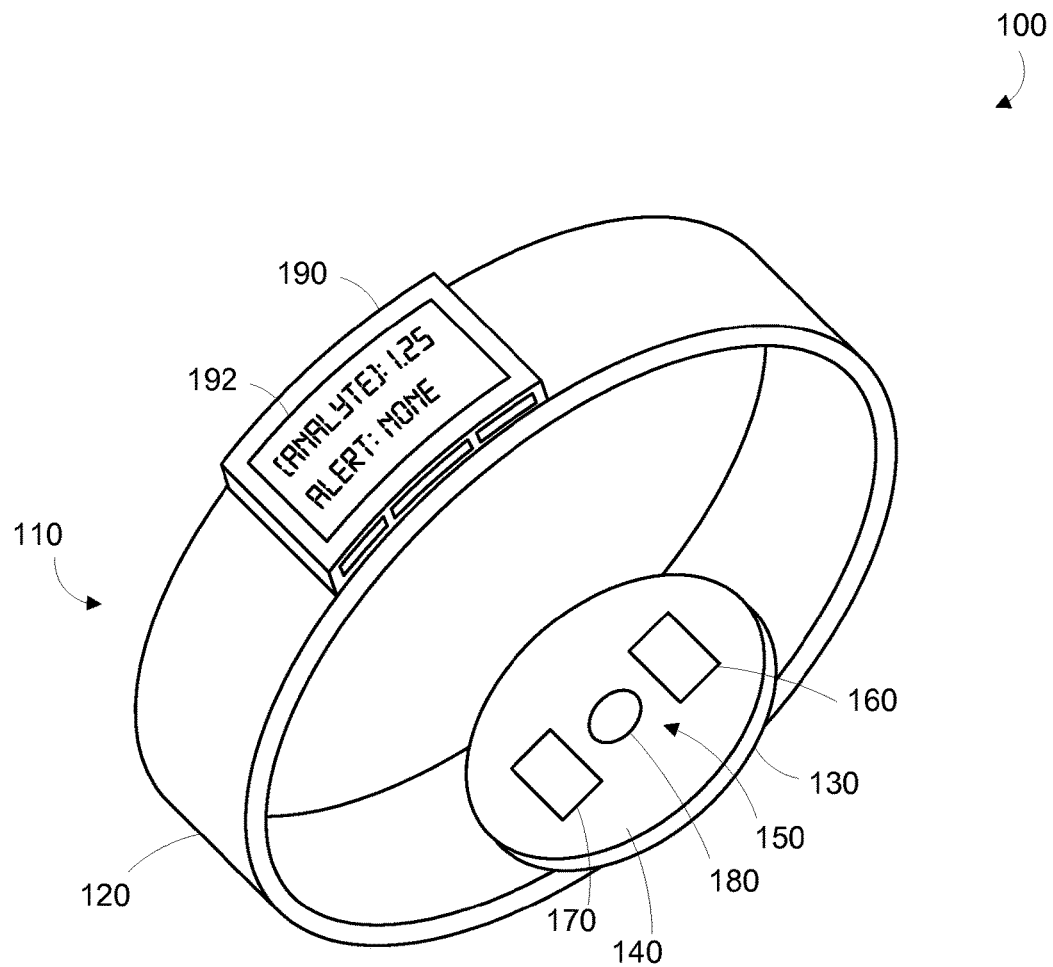
FIG. 1 is a perspective view of an example wearable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

A wearable device can automatically detect and measure a plurality of physiological parameters of a person wearing the device. The physiological parameters could include any parameters that may relate to the health of the person wearing the wearable device. For example, the wearable device could include sensors for measuring blood pressure, pulse rate, skin temperature, etc. At least some of the physiological parameters may be obtained by the wearable device non-invasively detecting and/or measuring one or more analytes in blood circulating in subsurface vasculature proximate to the wearable device. The one or more analytes could be any analytes that, when present in or absent from the blood, or present at a particular concentration or range of concentrations, may be indicative of a medical condition or health of the person wearing the device. For example, the one or more analytes could include enzymes, hormones, proteins, cells or other molecules.

The wearable device can include a mount that is configured to mount the device to a specific surface of the person's body, more particularly, to a body location where subsurface vasculature is readily observable. For example, the wearable device can include a wristband for mounting the wearable device on the wrist. In this position, the wearable device may be only about 2-4 millimeters away from the midpoint of an artery, capillary or vein in the wrist.

In an example embodiment, the wearable device obtains at least some of the health-related information by detecting the binding of a clinically-relevant analyte to functionalized particles, for example, microparticles or nanoparticles introduced into a lumen of the subsurface vasculature. The term "binding" is understood in its broadest sense to also include a detectable interaction between the clinically relevant analyte and the functionalized particles. The particles can have a diameter that is less than about 20 micrometers. In some embodiments, the particles have a diameter on the order of about 10 nm to 1 μm. In further embodiments, small particles on the order of 10-100 nm in diameter may be assembled to form a larger "clusters" or "assemblies on the order of 1-10 micrometers. Those of skill in the art will understand a "particle" in its broadest sense and that it may take the form of any fabricated material, a molecule, cryptophan, a virus, a phage, etc. Further, a particle may be of any shape, for example, spheres, rods, non-symmetrical shapes, etc.

In some examples, the particles may be magnetic and can be formed from a paramagnetic, super-paramagnetic or ferromagnetic material or any other material that responds to a magnetic field. Alternatively, the particles may also be made of non-magnetic materials such as polystyrene.

The particles, or a group of several particles in a complex, may be functionalized with a receptor that has a specific affinity to bind to or interact with a clinically relevant analyte. The receptor may be inherent to the particle itself. For example, the particle itself may be a virus or a phage with an inherent affinity for certain analytes. Additionally or alternatively, the particles can be functionalized by covalently attaching a receptor that specifically binds or otherwise recognizes a particular clinically-relevant analyte. The functionalized receptor can be an antibody, peptide, nucleic acid, phage, bacteria, virus, or any other molecule with a defined affinity for a target analyte. Other compounds or molecules, such as fluorophores or autofluorescent or luminescent markers, which may assist in interrogating the particles in vivo, may also be attached to the particles.

The functionalized particles can be introduced into the person's blood stream by injection, ingestion, inhalation, transdermally, or in some other manner. Where magnetic particles are used, the wearable device may include a magnet that can direct into the portion of subsurface vasculature a magnetic field that is sufficient to cause the functionalized magnetic particles to collect in a lumen of that portion of subsurface vasculature. However, measurements may be taken without localized "collection" of the functionalized particles. The wearable device may be configured to activate the magnetic periodically, such as at certain times of every day (e.g., every hour).

The wearable device may further include one or more data collection systems for interrogating, in a non-invasive manner, the functionalized particles present in a lumen of the subsurface vasculature in the local area of the wearable device. In one example, the wearable device includes a signal source for transmitting an interrogating signal that can penetrate the wearer's skin into the portion of subsurface vasculature and a detector for detecting a response signal that is transmitted from the portion of subsurface vasculature in response to the interrogating signal. The interrogating signal can be any kind of signal that is benign to the wearer and results in a response signal that can be used to detect binding of the clinically-relevant analyte to the functionalized particles. In one example, the interrogating signal is a radio frequency (RF) signal and the response signal is a magnetic resonance signal, such as nuclear magnetic resonance (NMR). In another example, where the functionalized particles include a fluorophore, the interrogating signal is an optical signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

Further, in some cases, an interrogating signal may not be necessary to produce a response signal. For example, where the functionalized particles include an autofluorescent or luminescent marker, an interrogating signal may not be necessary. In some examples, the functionalized particles may include a chemo-luminescent marker configured to produce a response signal in the form of fluorescence radiation produced in response to a chemical reaction initiated, at least in part, to the binding of the target analyte to the particle.

The wearable device can also include one or more data collection systems that do not make use of functionalized particles. For example, the wearable device can include sensors for measuring blood pressure, pulse rate, skin temperature, or other parameters. If in the form of a wristband, the wearable device may also include a watch face for displaying the time and/or date.

In addition, the wearable device may be configured to analyze the data that it collects. For example, the wearable device may include a computing device that is configured to detect the presence or absence of the clinically-relevant analyte and, in some examples, to further determine a concentration of the clinically-relevant analyte based on the response signal detected by the detector and determine whether a medical condition is indicated based on at least the presence, absence and/or concentration of the clinically-relevant analyte. In some examples, a medical condition may be indicated based, at least in part, on the fact that a particular clinically-relevant analyte is absent from the blood or is present in the blood at a lower than normal concentration, such as when a target analyte is being taken up by a tumor. The wearable device may be configured to conduct such an "inverse" test by recognizing that a particular class of functionalized particles does not produce a responsive signal proportional to the amount of that class of particles introduced into a lumen of the vasculature. The wearable device may also include a user interface that can display the results of the data analysis, such as whether the clinically-relevant analyte is present and in what concentration. In this way, the person wearing the device can be made aware of medical conditions in real time. The wearable device may also be configured to produce an auditory or tactile (vibration) response to alert the person wearing the device of a medical condition.

The wearable device may further include a communication interface for transmitting the results of the data analysis to medical personnel and/or receiving instructions or recommendations based on a medical personnel or remote computing device's interpretation of those results. In some examples, the communication interface is a wireless communication interface. The communication interface may also include a universal serial bus (USB) interface, a secure digital (SD) card interface, a wired interface, or any other appropriate interface for communicating data from the device to a server. The term "server" may include any system or device that responds to requests across a computer network to provide, or helps to provide, a network service, and may include servers run on dedicated computers, mobile devices and those operated in a cloud computing network.

As one possible example, the presence of an unstable arterial plaque that could potentially cause a heart attack or stroke is often associated with an increase in certain protein markers in the blood. A person who may be at risk for this medical condition may take particles that are functionalized to bind to such protein markers and may wear on his or her wrist a device that is configured to periodically (e.g., every hour) collect and interrogate the functionalized particles to determine the concentrations of the protein markers. If the device determines that the concentrations of the protein markers indicate an elevated risk of a heart attack or other life-threatening episode, the device may generate an alert through the user interface (e.g., an audible alarm) so that the person wearing the device can seek immediate medical attention.

The wearable device may obtain data in each of a plurality of measurement periods. The length of the measurement period may be set on the device itself or may be set remotely, for example, by instruction from a remote server. The device may be configured with many measurement periods each day—for example, continuous, every second, every minute, every hour, every 6 hours, etc.—or may be configured to take measurements once a week or once a month. The measurement periods can extend through a plurality of consecutive days (such as 30 or more days), and each of the consecutive days can include multiple measurement periods. In one example, the wearable device could measure the physiological parameters every hour, so that each of the consecutive days includes twenty-four measurement periods. In other examples, the wearable device could measure the physiological parameters more frequently or less frequently, or the wearable device could measure some of the physiological parameters more frequently than others.

Data representative of the physiological parameters may be used to develop an individual baseline profile for the wearer of the wearable device. The baseline profile may include patterns for how one or more of the wearer's physiological parameters typically change over time, such as during the course of a day, a week, or a month. The baseline profile may be developed on the wearable device itself (such as by a processor), or it may be developed by a remote server.

The wearable device may be configured to transmit certain data, such as the data representative of the physiological parameters, the baseline profile, etc., to a server, for example, via a wireless communication interface in the wearable device. In this way, the server may receive from the wearable device data regarding the plurality of physiological parameters for each of the plurality of measurement periods. The wearable device may be configured to automatically transmit the data to a server, may be configured to transmit on command of the wearer, or may be configured to transmit on instruction from a remote server. Further, the device may be configured to automatically transmit the data at the end of each measurement period, or at some more frequent or infrequent rate. For example, the device could be configured to transmit every five minutes, at the end of each day, at the end of the month, at nighttime only, etc.

After a baseline profile for a wearer of the device has been developed, either by the device or the server, additional data regarding the physiological parameters may be collected over additional measurement periods by the wearable device and may be compared to the baseline profile. Such comparison may be carried out on the wearable device itself, or by a remote server upon transmission of the additional data to the server. If the additional data is consistent with the patterns embodied in the baseline profile, the server may determine that the wearer's condition has not changed. On the other hand, if the additional data deviates from the patterns embodied in the baseline profile, the server may determine that the wearer's condition has changed. The change in condition could, for example, indicate that the wearer has developed a disease, disorder, or other adverse medical condition or may be at risk for a severe medical condition, such as a stroke or a heart attack, in the near future.

When a change in condition is detected, a clinical protocol may be consulted to generate one or more recommendations that are appropriate for the wearer's change in condition. For example, a recommendation that the wearer take a particular medication or supplement, schedule an appointment with a medical professional, go to the hospital to seek immediate medical attention, abstain from certain activities, etc. may be generated. The clinical protocol may be developed based, at least in part, on correlations between analyte concentration and health state of the wearer of the device, any known health information or medical history of the wearer, and/or on recognized standards of care in the medical field. Such actions may be carried out by a processor on the wearable device, or by a remote server.

Further, the wearable device may be configured to accept inputs from the wearer regarding his or her health state. The inputs may be subjective indicia regarding how the person is feeling or any symptoms he or she is experiencing at that time, such as, "feeling cold," "feeling tired," "stressed,"

"feeling rested and energetic," "pollen allergy symptoms today," etc. Such inputs from the user may be used to complement the physiological parameter data and establish correlations between the blood analysis results and health state.

The wearable device may be configured to accept, or the server may be configured to receive from some other source, certain environmental information. For example, information regarding the general health state of the population, such as when influenza or other viral outbreak has occurred, may be input into the system. Further, other general information that may affect the health of the population, such as daily pollen counts, pollution levels or the weather conditions may be input into the system. Such information may further be used to complement the physiological parameter data collected from individual wearers and populations of wearers of the device and establish correlations between the blood analysis results, health state and environmental factors.

Once generated, either by the server or the wearable device itself, the wearable device may provide an indication of the one or more recommendations via a user interface on the wearable device. The indication could be any indication that can be noticed by the person wearing the wearable device. For example, the indication could include a visual component (e.g., textual or graphical information on a display), an auditory component (e.g., an alarm sound), and/or tactile component (e.g., a vibration).

The wearable device and/or the server may also be configured to receive information regarding the actual health state of the wearer of the wearable device. This information may be received at the end of each analyte measurement period, or at some other frequency. In one example, the wearable device itself, or some external computing device, may be configured to accept such information as inputs and transmit it to the server or medical professional(s). Further, the wearable device and/or the server may be configured to derive correlations between the reported health state of the wearer, and the blood analyte measurement(s) transmitted by the wearable device. For example, the wearable device and/or the server may analyze the blood analyte data and the health state data and detect that the wearer has experienced certain adverse health conditions, such as a migraine or a heart attack, when an analyte reached a certain concentration. The wearable device and/or the server may use this correlation data to generate recommendations for the wearer, or to develop a clinical protocol.

The server that receives the data from the wearable device may receive similar data from a plurality of other, similar wearable devices. In this way, the server can collect data regarding a plurality of human subjects. This data, including both the analyte measurements and the indications of health state, may, in turn, be used to develop one or more clinical protocols used by the server to generate recommendations and/or used by medical professionals to provide medical care and advice to their patients. This data may further be used to recognize correlations between blood analytes and health conditions among the population. Health professionals may further use this data to diagnose and prevent illness and disease, prevent serious clinical events in the population, and to update clinical protocols, courses of treatment, and the standard of care.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. EXAMPLE WEARABLE DEVICES

A wearable device 100 can automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 110, such as a belt, wristband, ankle band, etc. can be provided to mount the device at, on or in proximity to the body surface. The mount 110 may prevent the wearable device from moving relative to the body to reduce measurement error and noise. In one example, shown in FIG. 1, the mount 110, may take the form of a strap or band 120 that can be worn around a part of the body. Further, the mount 110 may be an adhesive substrate for adhering the wearable device 100 to the body of a wearer.

A measurement platform 130 is disposed on the mount 110 such that it can be positioned on the body where subsurface vasculature is easily observable. An inner face 140 of the measurement platform is intended to be mounted facing to the body surface. The measurement platform 130 may house the data collection system 150, which may include at least one detector 160 for detecting at least one physiological parameter, which could include any parameters that may relate to the health of the person wearing the wearable device. For example, the detector 160 could be configured to measure blood pressure, pulse rate, respiration rate, skin temperature, etc. At least one of the detectors 160 is configured to non-invasively measure one or more analytes in blood circulating in subsurface vasculature proximate to the wearable device. In a non-exhaustive list, detector 160 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the data collection system 150 may be miniaturized so that the wearable device may be worn on the body without significantly interfering with the wearer's usual activities.

In some examples, the data collection system 150 further includes a signal source 170 for transmitting an interrogating signal that can penetrate the wearer's skin into the portion of subsurface vasculature, for example, into a lumen of the subsurface vasculature. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the functionalized particles. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the particles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In some examples, the functionalized particles include a fluorophore. The interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

In some cases, an interrogating signal is not necessary to measure one or more of the physiological parameters and, therefore, the wearable device 100 may not include a signal source 170. For example, the functionalized particles include an autofluorescent or luminescent marker, such as a fluorophore, that will automatically emit a response signal indicative of the binding of the clinically-relevant analyte to the functionalized particles, without the need for an interrogating signal or other external stimulus. In some examples, the functionalized particles may include a chemoluminescent marker configured to produce a response signal in the form of fluorescence radiation produced in response to a chemical reaction initiated, at least in part, to the binding of the target analyte to the particle.

A collection magnet 180 may also be included in the data collection system 150. In such embodiments, the functionalized particles may also be made of or be functionalized with magnetic materials, such as ferromagnetic, paramagnetic, super-paramagnetic, or any other material that responds to a magnetic field. The collection magnet 180 is configured to direct a magnetic field into the portion of subsurface vasculature that is sufficient to cause functionalized magnetic particles to collect in a lumen of that portion of subsurface vasculature. The magnet may be an electromagnet that may be turned on during measurement periods and turned off when a measurement period is complete so as to allow the magnetic particles to disperse through the vasculature.

The wearable device 100 may also include a user interface 190 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 190 may include a display 192 where a visual indication of the alert or recommendation may be displayed. The display 192 may further be configured to provide an indication of the measured physiological parameters, for instance, the concentrations of certain blood analytes being measured.

Figure 2A:
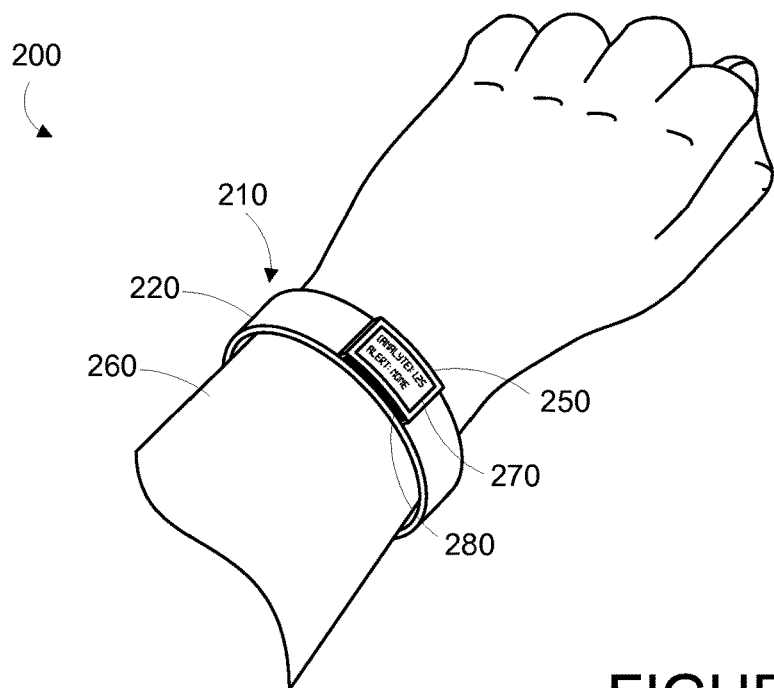
FIG. 2A is a perspective top view of an example wrist-mounted device, when mounted on a wearer's wrist.
Figure 2B:
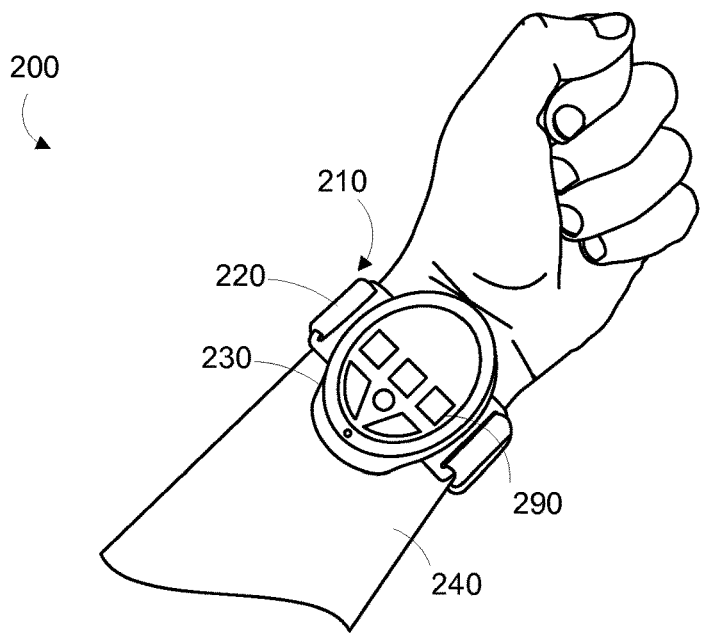
FIG. 2B is a perspective bottom view of an example wrist-mounted device shown in FIG. 2A, when mounted on a wearer's wrist.

In one example, the wearable device is provided as a wrist-mounted device, as shown in FIGS. 2A, 2B, 3A-3C, 4A, 5B, 6 and 7. The wrist-mounted device may be mounted to the wrist of a living subject with a wristband or cuff, similar to a watch or bracelet. As shown in FIGS. 2A and 2B, the wrist mounted device 200 may include a mount 210 in the form of a wristband 220, a measurement platform 230 positioned on the anterior side 240 of the wearer's wrist, and a user interface 250 positioned on the posterior side 260 of the wearer's wrist. The wearer of the device may receive, via the user interface 250, one or more recommendations or alerts generated either from a remote server or other remote computing device, or alerts from the measurement platform. Such a configuration may be perceived as natural for the wearer of the device in that it is common for the posterior side 260 of the wrist to be observed, such as the act of checking a wrist-watch. Accordingly, the wearer may easily view a display 270 on the user interface. Further, the measurement platform 230 may be located on the anterior side 240 of the wearer's wrist where the subsurface vasculature may be readily observable. However, other configurations are contemplated.

The display 270 may be configured to display a visual indication of the alert or recommendation and/or an indication of the measured physiological parameters, for instance, the concentrations of certain blood analytes being measured. Further, the user interface 250 may include one or more buttons 280 for accepting inputs from the wearer. For example, the buttons 280 may be configured to change the text or other information visible on the display 270. As shown in FIG. 2B, measurement platform 230 may also include one or more buttons 290 for accepting inputs from the wearer. The buttons 290 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 3A:
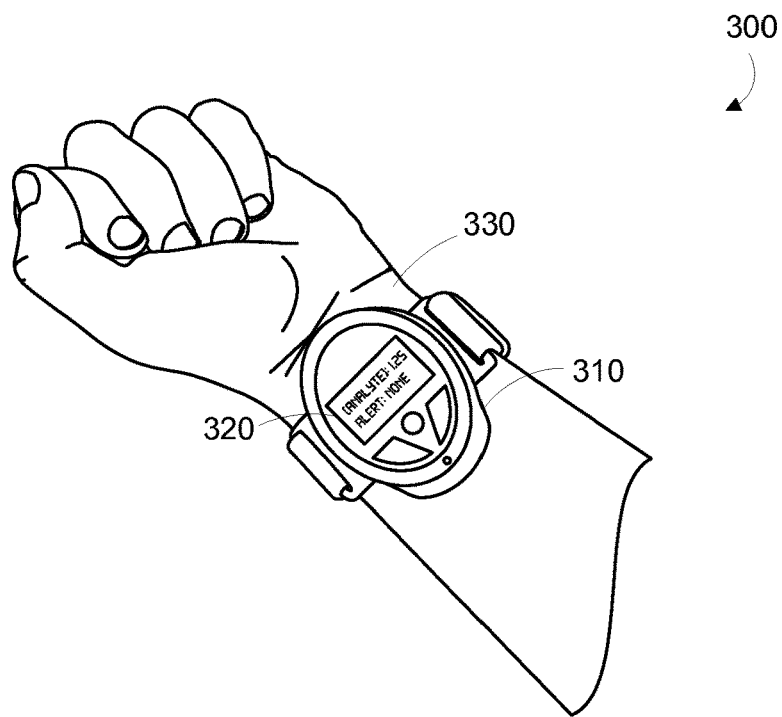
FIG. 3A is a perspective bottom view of an example wrist-mounted device, when mounted on a wearer's wrist.
Figure 3B:
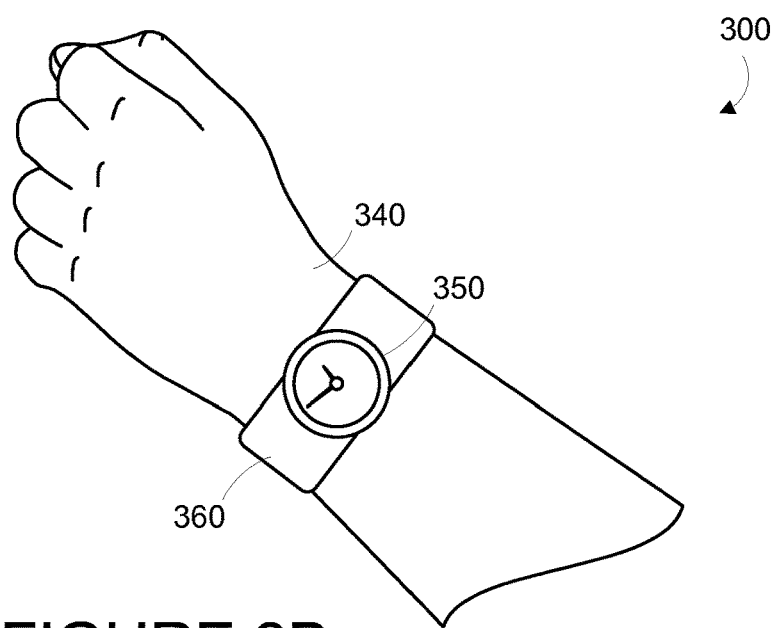
FIG. 3B is a perspective top view of an example wrist-mounted device shown in FIG. 3A, when mounted on a wearer's wrist.
Figure 3C:
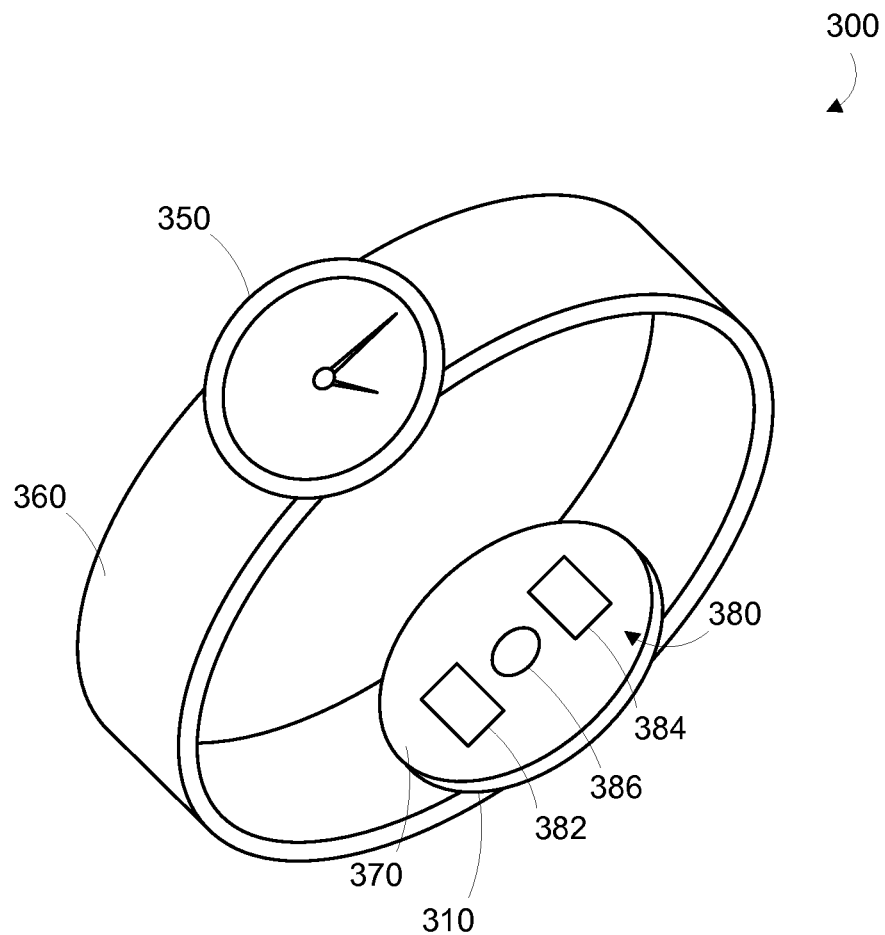
FIG. 3C is a perspective view of an example wrist-mounted device shown in FIGS. 3A and 3B.

In another example wrist-mounted device 300, shown in FIGS. 3A-3C, the measurement platform 310 and user interface 320 are both provided on the same side of the wearer's wrist, in particular, the anterior side 330 of the wrist. On the posterior side 340, a watch face 350 may be disposed on the strap 360. While an analog watch is depicted in FIG. 3B, one of ordinary skill in the art will recognize that any type of clock may be provided, such as a digital clock.

As can be seen in FIG. 3C, the inner face 370 of the measurement platform 310 is intended to be worn proximate to the wearer's body. A data collection system 380 housed on the measurement platform 310 may include a detector 382, a signal source 384 and a collection magnet 386. As described above, the signal source 384 and the collection magnet 386 may not be provided in all embodiments of the wearable device.

Figure 4A:
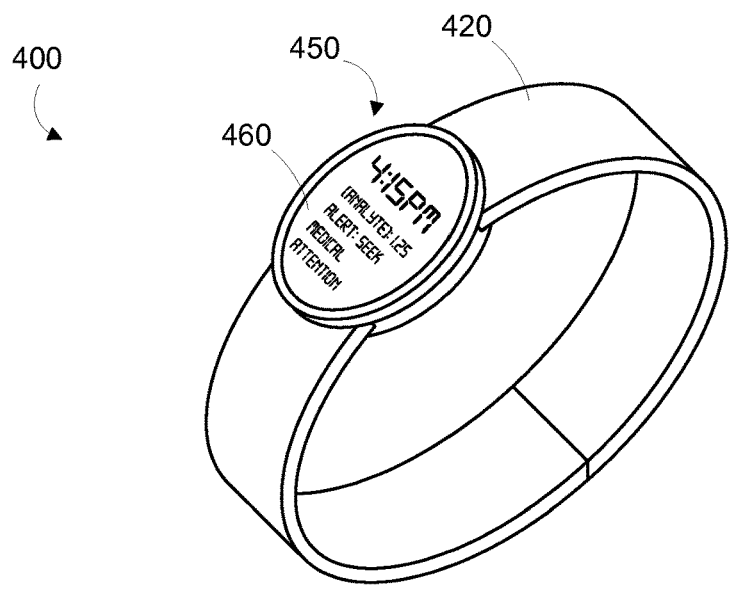
FIG. 4A is a perspective view of an example wrist-mounted device.
Figure 4B:
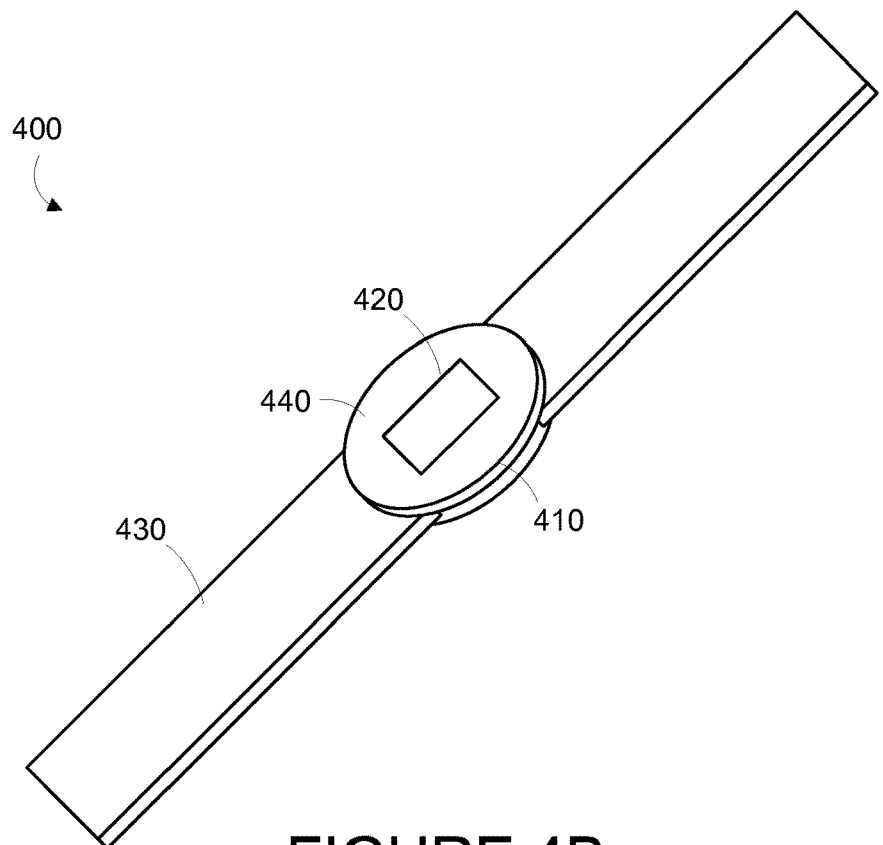
FIG. 4B is a perspective bottom view of an example wrist-mounted device shown in FIG. 4A.

In a further example shown in FIGS. 4A and 4B, a wrist mounted device 400 includes a measurement platform 410, which includes a data collection system 420, disposed on a strap 430. Inner face 440 of measurement platform may be positioned proximate to a body surface so that data collection system 420 may interrogate the subsurface vasculature of the wearer's wrist. A user interface 450 with a display 460 may be positioned facing outward from the measurement platform 410. As described above in connection with other embodiments, user interface 450 may be configured to display data collected from the data collection system 420, including the concentration of one or more measured analytes, and one or more alerts generated by a remote server or other remote computing device, or a processor located on the measurement platform. The user interface 420 may also be configured to display the time of day, date, or other information that may be relevant to the wearer.

Figure 5:
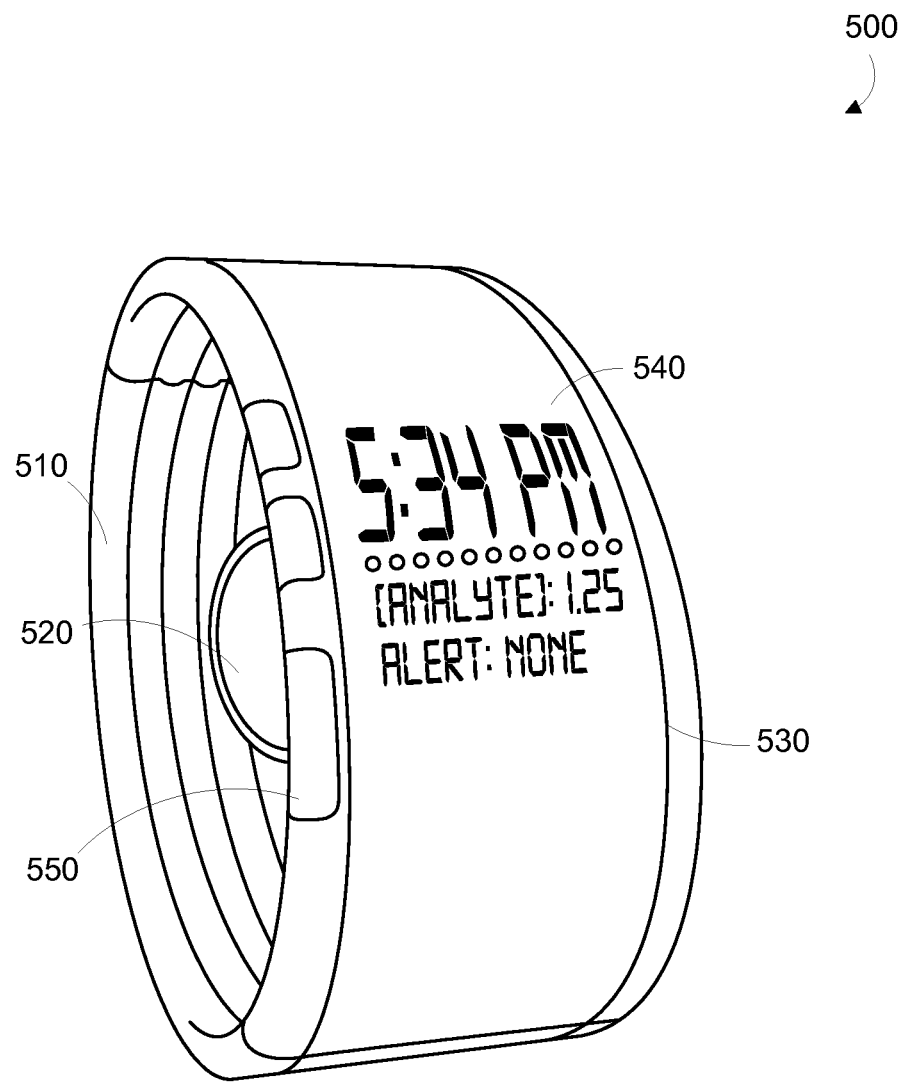
FIG. 5 is a perspective view of an example wrist-mounted device.
Figure 6:
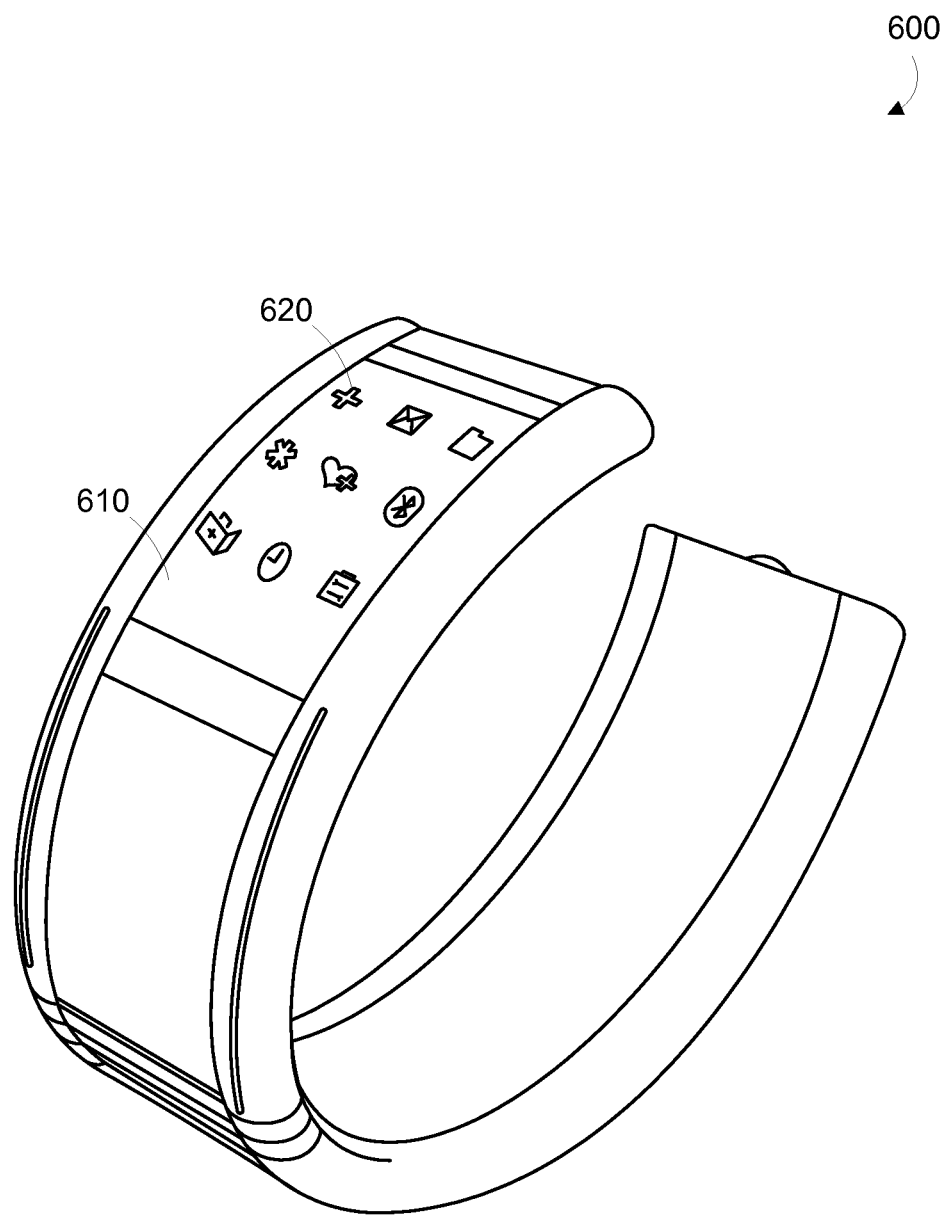
FIG. 6 is a perspective view of an example wrist-mounted device.

As shown in FIG. 5, in a further embodiment, wrist-mounted device 500 may be provided on a cuff 510. Similar to the previously discussed embodiments, device 500 includes a measurement platform 520 and a user interface 530, which may include a display 540 and one or more buttons 550. The display 540 may further be a touch-screen display configured to accept one or more input by the wearer. For example, as shown in FIG. 6, display 610 may be a touch-screen configured to display one or more virtual buttons 620 for accepting one or more inputs for controlling certain functions or aspects of the device 600, or inputs of information by the user, such as current health state.

Figure 7:
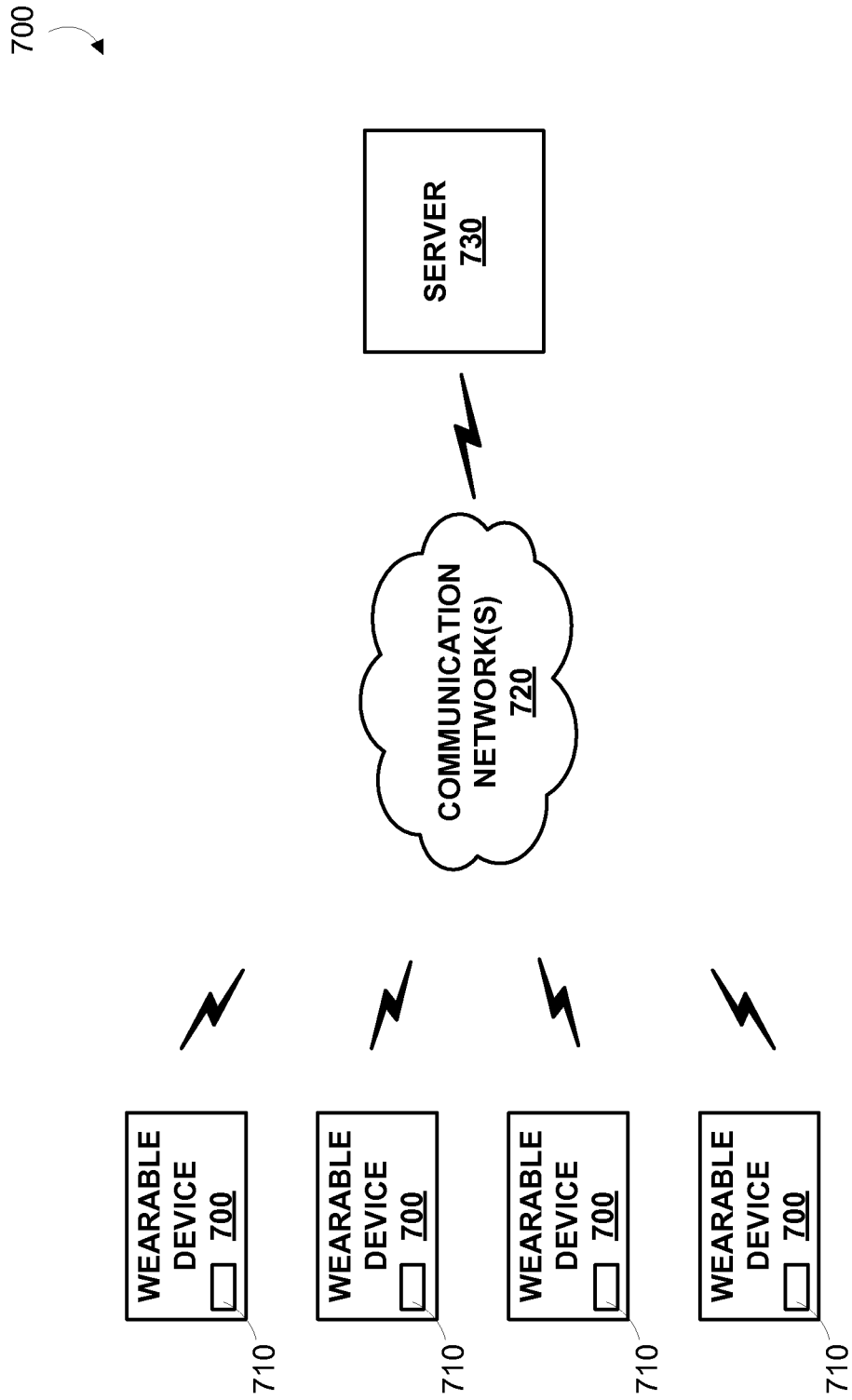
FIG. 7 is a block diagram of an example system that includes a plurality of wrist mounted devices in communication with a server.

FIG. 7 is a simplified schematic of a system including one or more wearable devices 700. The one or more wearable devices 700 may be configured to transmit data via a communication interface 710 over one or more communication networks 720 to a remote server 730. In one embodiment, the communication interface 710 includes a wireless transceiver for sending and receiving communications to and from the server 730. In further embodiments, the communication interface 710 may include any means for the transfer of data, including both wired and wireless communications. For example, the communication interface may include a universal serial bus (USB) interface or a secure digital (SD) card interface. Communication networks 720 may be any one of may be one of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 700 transmits data to a mobile phone or other personal computing device, which in turn transmits the data to the server 730.

In addition to receiving communications from the wearable device 700, such as collected physiological parameter data and data regarding health state as input by the user, the server may also be configured to gather and/or receive either from the wearable device 700 or from some other source, information regarding a wearer's overall medical history, environmental factors and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

III. EXAMPLE ELECTRONICS PLATFORM FOR A WEARABLE DEVICE

Figure 8:
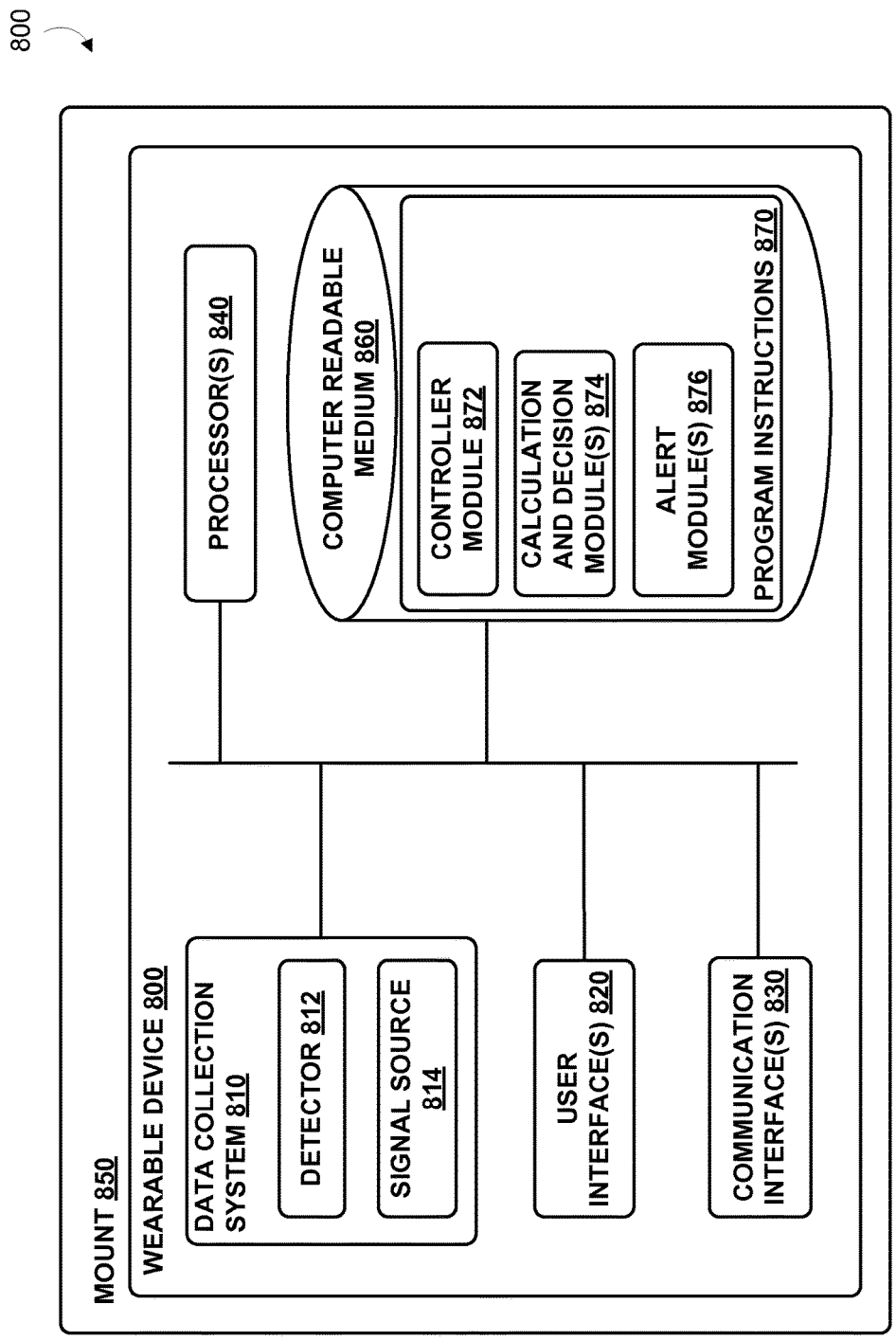
FIG. 8 is a functional block diagram of an example wearable device.

FIG. 8 is a simplified block diagram illustrating the components of a wearable device 800, according to an example embodiment. Wearable device 800 may take the form of or be similar to one of the wrist-mounted devices 200, 300, 400, 500, 600, shown in FIGS. 2A-B, 3A-3C, 4A-4C, 5 and 6. However, wearable device 800 may also take other forms, such as an ankle, waist, or chest-mounted device.

In particular, FIG. 7 shows an example of a wearable device 800 having a data collection system 810, a user interface 820, communication platform 830 for transmitting data to a server, and processor(s) 840. The components of the wearable device 800 may be disposed on a mount 850 for mounting the device to an external body surface where a portion of subsurface vasculature is readily observable.

Processor 840 may be a general-purpose processor or a special purpose processor (e.g., digital signal processors, application specific integrated circuits, etc.). The one or more processors 840 can be configured to execute computer-readable program instructions 870 that are stored in the computer readable medium 860 and are executable to provide the functionality of a wearable device 800 described herein.

The computer readable medium 860 may include or take the form of one or more non-transitory, computer-readable storage media that can be read or accessed by at least one processor 840. The one or more computer-readable storage media can include volatile and/or non-volatile storage components, such as optical, magnetic, organic or other memory or disc storage, which can be integrated in whole or in part with at least one of the one or more processors 840. In some embodiments, the computer readable medium 860 can be implemented using a single physical device (e.g., one optical, magnetic, organic or other memory or disc storage unit), while in other embodiments, the computer readable medium 860 can be implemented using two or more physical devices.

Data collection system 810 includes a detector 812 and, in some embodiments, a signal source 814. As described above, detector 812 may include any detector capable of detecting at least one physiological parameter, which could include any parameters that may relate to the health of the person wearing the wearable device. For example, the detector 812 could be configured to measure blood pressure, pulse rate, skin temperature, etc. At least one of the detectors 812 is configured to non-invasively measure one or more analytes in blood circulating in subsurface vasculature proximate to the wearable device. In some examples, detector 812 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

In some examples, the data collection system 810 further includes a signal source 814 for transmitting an interrogating signal that can penetrate the wearer's skin into the portion of subsurface vasculature. In general, signal source 814 will generate an interrogation signal that will produce a responsive signal that can be detected by one or more of the detectors 812. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the functionalized particles. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the particles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In examples where the functionalized particles include a fluorophore, the interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

The program instructions 870 stored on the computer readable medium 860 may include instructions to perform or facilitate some or all of the device functionality described herein. For instance, in the illustrated embodiment, program instructions 870 include a controller module 872, calculation and decision module 874 and an alert module 876.

The controller module 872 can include instructions for operating the data collection system 810, for example, the detector 812 and signal source 814. For example, the controller 872 may activate signal source 814 and/or detector 812 during each of the pre-set measurement periods. In particular, the controller module 872 can include instructions for controlling the signal source 814 to transmit an interrogating signal at preset measurement times and controlling the detector 812 to receive data representative of response signals transmitted from the portion of subsurface vasculature in response to the interrogating signals transmitted at the preset measurement times.

The controller module 872 can also include instructions for operating a user interface 820. For example, controller module 872 may include instructions for displaying data collected by the data collection system 810 and analyzed by the calculation and decision module 874, or for displaying one or more alerts generated by the alert module 875. Further, controller module 872 may include instructions to execute certain functions based on inputs accepted by the user interface 820, such as inputs accepted by one or more buttons disposed on the user interface.

Communication interface 730 may also be operated by instructions within the controller module 872, such as instructions for sending and/or receiving information via a wireless antenna, which may be disposed on or in the wearable device 800. The communication interface 830 can optionally include one or more oscillators, mixers, frequency injectors, etc. to modulate and/or demodulate information on a carrier frequency to be transmitted and/or received by the antenna. In some examples, the wearable device 800 is configured to indicate an output from the processor by modulating an impedance of the antenna in a manner that is perceivable by a remote server or other remote computing device.

Calculation and decision module 872 may include instructions for receiving data from the data collection system 810 in the form of a responsive signal, analyzing the data to determine if the target analyte is present or absent, quantify the measured physiological parameter(s), such as concentration of a target analyte, and analyzing the data to determine if a medical condition is indicated. In particular, the calculation and decision module 872 may include instructions for determining, for each preset measurement time, a concentration of a clinically-relevant analyte based on the response signal detected by the detector at that measurement time and determining, for each preset measurement time, whether a medical condition is indicated based on at least the corresponding concentration of the clinically-relevant analyte. The preset measurement times may be set to any period and, in one example, are about one hour apart.

The program instructions of the calculation and decision module 872 may, in some examples, be stored in a computer-readable medium and executed by a processor located external to the wearable device. For example, the wearable device could be configured to collect certain data regarding physiological parameters from the wearer and then transmit the data to a remote server, which may include a mobile device, a personal computer, the cloud, or any other remote system, for further processing.

The computer readable medium 860 may further contain other data or information, such as medical and health history of the wearer of the device, that may be necessary in determining whether a medical condition is indicated. Further, the computer readable medium 860 may contain data corresponding to certain analyte baselines, above or below which a medical condition is indicated. The baselines may be pre-stored on the computer readable medium 860, may be transmitted from a remote source, such as a remote server, or may be generated by the calculation and decision module 874 itself. The calculation and decision module 874 may include instructions for generating individual baselines for the wearer of the device based on data collected over a certain number of measurement periods. For example, the calculation and decision module 874 may generate a baseline concentration of a target blood analyte for each of a plurality of measurement periods by averaging the analyte concentration at each of the measurement periods measured over the course of a few days, and store those baseline concentrations in the computer readable medium 860 for later comparison. Baselines may also be generated by a remote server and transmitted to the wearable device 800 via communication interface 830. The calculation and decision module 874 may also, upon determining that a medical condition is indicated, generate one or more recommendations for the wearer of the device based, at least in part, on consultation of a clinical protocol. Such recommendations may alternatively be generated by the remote server and transmitted to the wearable device.

In some examples, the collected physiological parameter data, baseline profiles, health state information input by device wearers and generated recommendations and clinical protocols may additionally be input to a cloud network and be made available for download by a wearer's physician. Trend and other analyses may also be performed on the collected data, such as physiological parameter data and health state information, in the cloud computing network and be made available for download by physicians or clinicians.

Further, physiological parameter and health state data from individuals or populations of device wearers may be used by physicians or clinicians in monitoring efficacy of a drug or other treatment. For example, high-density, real-time data may be collected from a population of device wearers who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 874 that a medical condition is indicated, the alert module 876 may generate an alert via the user interface 820. The alert may include a visual component, such as textual or graphical information displayed on a display, an auditory component (e.g., an alarm sound), and/or tactile component (e.g., a vibration). The textual information may include one or more recommendations, such as a recommendation that the wearer of the device contact a medical professional, seek immediate medical attention, or administer a medication.

Figure 9:
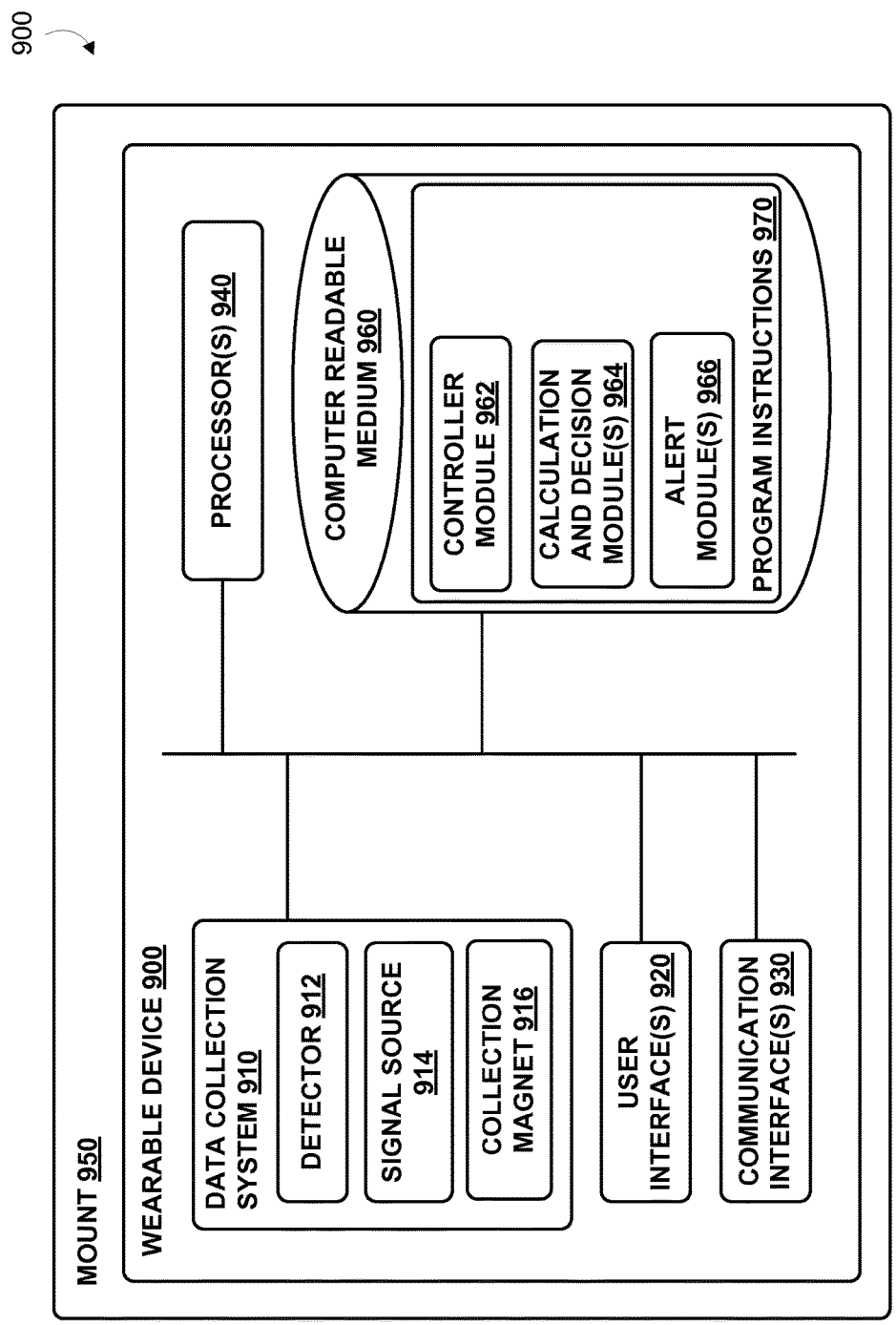
FIG. 9 is a functional block diagram of an example wearable device.

FIG. 9 is a simplified block diagram illustrating the components of a wearable device 900, according to an example embodiment. Wearable device 900 is the same as wearable device 800 in all respects, except that the data collection system 910 of wearable device 900 further includes a collection magnet 916. In this example, the collection magnet 916 may be used to locally collect functionalized magnetic particles present in an area of subsurface vasculature proximate to the collection magnet 916. As described above, collection magnet 916 is configured to direct a magnetic field into a portion of subsurface vasculature sufficient to cause functionalized magnetic particles to collect in a lumen of the portion of subsurface vasculature.

Wearable device 900 includes a data collection system 910, which includes a detector 912, a signal source 914 (if provided) and a collection magnet 916, a user interface 920, a communication interface 930, a processor 940 and a computer readable medium 960 on which program instructions 970 are stored. All of the components of wearable device 900 may be provided on a mount 950. In this example, the program instructions 970 may include a controller module 962, a calculation and decision module 964 and an alert module 966 which, similar to the example set forth in FIG. 8, include instructions to perform or facilitate some or all of the device functionality described herein. Controller module 962 further includes instructions for operating collection magnet 916. For example, controller module 962 may include instructions for activating collection magnet during a measurement period, for a certain amount of time.

III. ILLUSTRATIVE FUNCTIONALIZED PARTICLES

In some examples, the wearable devices described above obtain at least some of the health-related information by detecting the binding of a clinically-relevant analyte to functionalized particles, for example, microparticles or nanoparticles. The particles can be functionalized by covalently attaching a bioreceptor designed to selectively bind or otherwise recognize a particular clinically-relevant analyte. For example, particles may be functionalized with a variety of bioreceptors, including antibodies, nucleic acids (DNA, siRNA), low molecular weight ligands (folic acid, thiamine, dimercaptosuccinic acid), peptides (RGD, LHRD, antigenic peptides, internalization peptides), proteins (BSA, transferrin, antibodies, lectins, cytokines, fibrinogen, thrombin), polysaccharides (hyaluronic acid, chitosan, dextran, oligosaccharides, heparin), polyunsaturated fatty acids (palmitic acid, phospholipids), plasmids. The functionalized particles can be introduced into the person's blood stream by injection, ingestion, inhalation, transdermally, or in some other manner.

The clinically-relevant analyte could be any analyte that, when present in or absent from the blood, or present at a particular concentration or range of concentrations, may be indicative of a medical condition or indicative that a medical condition may be imminent. For example, the clinically-relevant analyte could be an enzyme, hormone, protein, or other molecule. In one relevant example, certain protein biomarkers are known to be predictive of an impending arterial plaque rupture. Such protein biomarkers are known to be present in the blood only directly leading up to and at the onset of an arterial plaque rupture. Plaques that rupture cause the formation of blood clots that can block blood flow or break off and travel to another part of the body. In either of these cases, if a clot blocks a blood vessel that feeds the heart, it causes a heart attack. If it blocks a blood vessel that feeds the brain, it causes a stroke. If blood supply to the arms or legs is reduced or blocked, it can cause difficulty walking and eventually gangrene. The presence of these protein biomarkers in the vasculature may be detected, and the medical condition (i.e., stroke, heart attack) prevented, by providing particles functionalized with a bioreceptor that will selectively bind to this target analyte.

The particles may be made of biodegradable or non-biodegradable materials. For example, the particles may be made of polystyrene. Non-biodegradable particles may be provided with a removal means to prevent harmful buildup in the body. Generally, the particles may be designed to have a long half-life so that they remain in the vasculature or body fluids over several measurement periods. Depending on the lifetime of the particles, however, the user of the wearable device may periodically introduce new batches of functionalized particles into the vasculature or body fluids.

Bioreceptors can be used in diagnostic procedures, or even in therapy to destroy a specific target, such as antitumor therapy or targeted chemotherapy. The particles may be designed to remove from the body or destroy the target analyte once bound to the bioreceptor. Additional functional groups may be added to the particles to signal that the particles can be removed from the body through the kidneys, for example, once bound to the target analyte.

Further, the particles may be designed to either releasably or irreversibly bind to the target analyte. For example, if it is desired for the particles to participate in destruction or removal of the target analyte from the body, as described above, the particles may be designed to irreversibly bind to the target analyte. In other examples, the particles may be designed to release the target analyte after measurement has been made, either automatically or in response to an external or internal stimulus.

Those of skill in the art will understand the term "particle" in its broadest sense and that it may take the form of any fabricated material, a molecule, cryptophan, a virus, a phage, etc. Further, a particle may be of any shape, for example, spheres, rods, non-symmetrical shapes, etc. The particles can have a diameter that is less than about 20 micrometers. In some embodiments, the particles have a diameter on the order of about 10 nm to 1 µm. In further embodiments, small particles on the order of 10-100 nm in diameter may be assembled to form a larger "clusters" or "assemblies on the order of 1-10 micrometers. In this arrangement, the assemblies would provide the signal strength of a larger particle, but would be deformable, thereby preventing blockages in smaller vessels and capillaries.

Binding of the functionalized particles to a target analyte may be detected with or without a stimulating signal input. The term "binding" is understood in its broadest sense to include any detectable interaction between the receptor and the target analyte. For example, some particles may be functionalized with compounds or molecules, such as fluorophores or autofluorescent, luminescent or chemo-luminescent markers, which generate a responsive signal when the particles bind to the target analyte without the input of a stimulus. In other examples, the functionalized particles may produce a different responsive signal in their bound versus unbound state in response to an external stimulus, such as an electromagnetic, acoustic, optical, or mechanical energy.

Further, the particles may be formed from a paramagnetic or ferromagnetic material or be functionalized with a magnetic moiety. The magnetic properties of the particles can be exploited in magnetic resonance detection schemes to enhance detection sensitivity. In another example, an external magnet may be used to locally collect the particles in an area of subsurface vasculature during a measurement period. Such collection may not only increase the differential velocity between particles and analytes, hence surveying a much larger volume per unit time, but may also enhance the signal for subsequent detection.

IV. ILLUSTRATIVE METHODS FOR OPERATION OF A WEARABLE DEVICE

Figure 10:
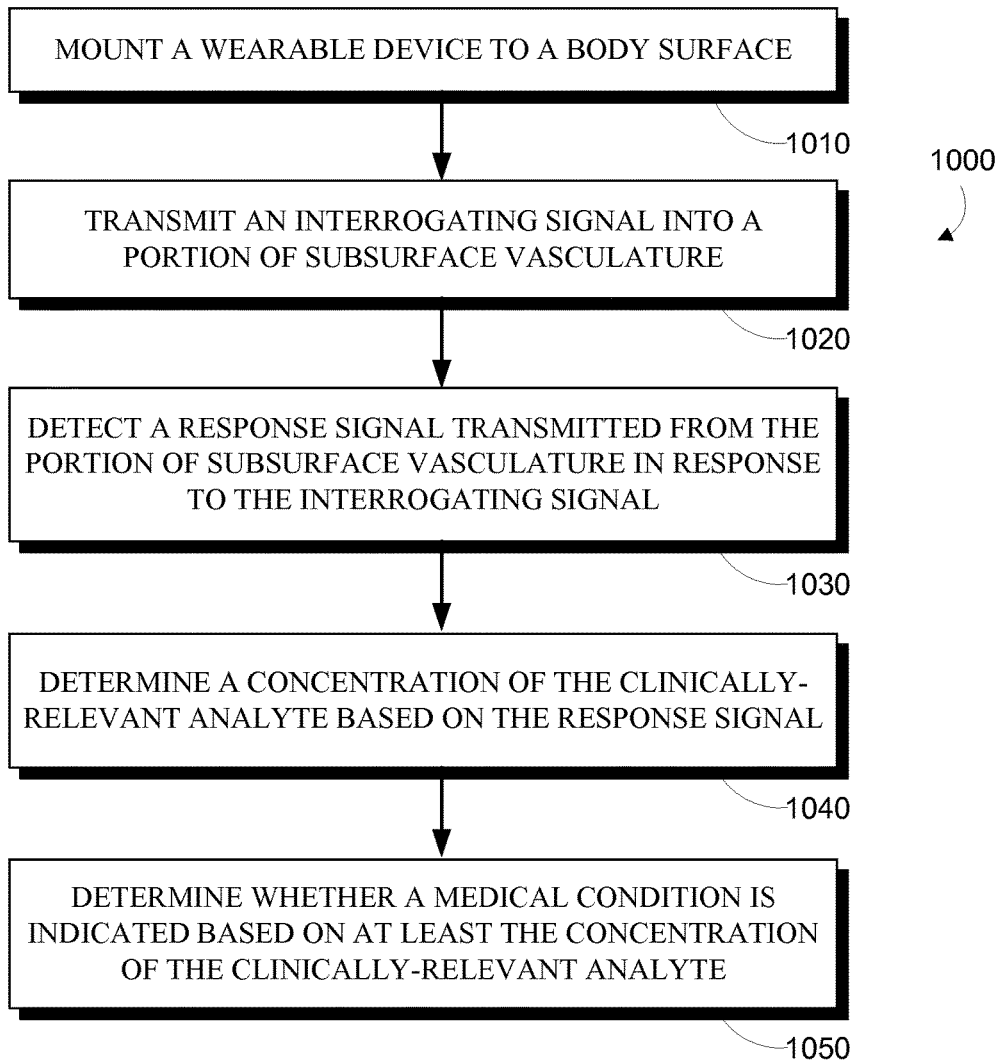
FIG. 10 is a flowchart of an example method for operating a wearable device.

FIG. 10 is a flowchart of a method 1000 for operating a wearable device to take non-invasive, in vivo, real-time measurements of physiological parameters. A wearable device is first mounted to a body surface of a human subject, wherein the body surface is proximate to a portion of subsurface vasculature (1010). In some examples, the wearable device, via a signal source, transmits an interrogating signal into the portion of subsurface vasculature (1020). The wearable device, via a detector, then detects a response signal transmitted from the portion of subsurface vasculature, wherein the response signal is related to binding of a clinically-relevant analyte to functionalized particles present in a lumen of the subsurface vasculature (1030). In some examples, the response signal is generated in response to an interrogating signal. The functionalized particles are configured to bind to the clinically-relevant analyte and may comprise a receptor, such as an antibody. The term "bind" is understood in its broadest sense to also include any detectable interaction between the clinically relevant analyte and the functionalized particles. The wearable device then determines the presence, absence and/or a concentration of the clinically-relevant analyte based on the response signal (1040) and whether a medical condition is indicated based on at least the presence, absence and/or concentration of the clinically-relevant analyte (1040). Further, in examples where the functionalized particles are magnetic, the wearable device may further direct a magnetic field into the portion of subsurface vasculature, the magnetic field being sufficient to cause the functionalized magnetic particles to collect in a lumen of the portion of subsurface vasculature.

Figure 11A:
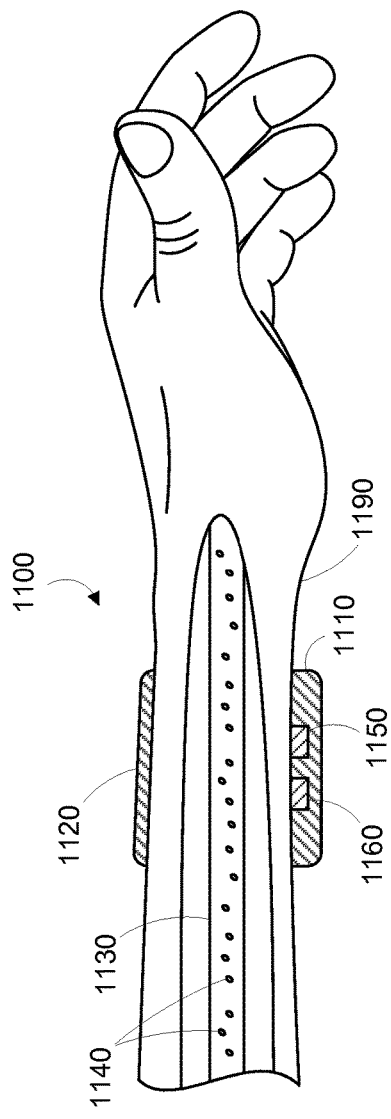
FIG. 11A is side partial cross-sectional view of a wrist-mounted device, while on a human wrist.
Figure 11B:
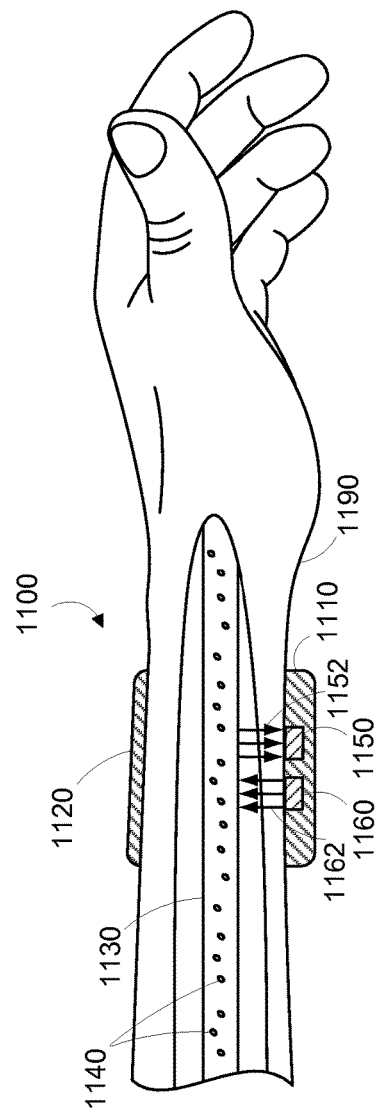
FIG. 11B is side partial cross-sectional view of a wrist-mounted device, while on a human wrist.

FIGS. 11A-11B, 12A-12B, and 13A-13B are partial cross-sectional side views of a human wrist illustrating the operation of various examples of a wrist-mounted device. In the example shown in FIGS. 11A and 11B, the wrist-mounted device 1100 includes a measurement platform 1110 mounted on a strap or wrist-band 1120 and oriented on the anterior side 1190 of the wearer's wrist. Measurement platform 1110 is positioned over a portion of the wrist where subsurface vasculature 1130 is easily observable. Functionalized particles 1140 have been introduced into a lumen of the subsurface vasculature by one of the means discussed above. In this example, measurement platform 1110 includes a data collection system having both a detector 1150 and a signal source 1160. FIG. 11A illustrates the state of the subsurface vasculature when measurement device 1100 is inactive. The state of the subsurface vasculature during a measurement period is illustrated in FIG. 11B. At this time, signal source 1160 is transmitting an interrogating signal 1162 into the portion of subsurface vasculature and detector 1150 is receiving a response signal 1152 generated in response to the interrogating signal 1162. The response signal 1152 is related to the binding of a clinically relevant analyte present in the subsurface vasculature to the functionalized particles 1140. As described above, in some embodiments, an interrogating signal may not be necessary to generate a response signal related to the binding of an analyte to the functionalized particles.

Similar to the system depicted in FIGS. 11A and 11B, FIGS. 12A and 12B illustrate a wrist-mounted device 1200 including a measurement platform 1210 mounted on a strap or wristband 1220 and oriented on the anterior side 1290 of the wearer's wrist. In this example, measurement platform 1210 includes a data collection system having a detector 1250, a signal source 1260 and a collection magnet 1270. FIG. 12A illustrates the state of the subsurface vasculature when measurement device 1200 is inactive. The state of the subsurface vasculature when measurement device 1200 is active during a measurement period is illustrated in FIG. 12B. At this time, collection magnet 1270 generates a magnetic field 1272 sufficient to cause functionalized magnetic particles 1240 present in a lumen of the subsurface vasculature 1230 to collection in a region proximal to the magnet 1270. Signal source 1260 transmits an interrogating signal 1262 into the portion of subsurface vasculature and detector 1250 is receiving a response signal 1252 generated in response to the interrogating signal 1262. The response signal 1252 is related to the binding of a clinically relevant analyte present in the subsurface vasculature to the functionalized magnetic particles 1240. As described above, in some embodiments, an interrogating signal may not be necessary to generate a response signal related to the binding of an analyte to the functionalized magnetic particles.

FIGS. 13A and 13B illustrate a further embodiment of a wrist-mounted device 1300 having a measurement platform 1310 disposed on a strap 1320, wherein the detector 1350 and signal source 1360 are positioned on the posterior side 1390 of the wearer's wrist and the collection magnet 1370 is disposed on the anterior side 1380 of the wearer's wrist. Similar to the embodiments discussed above, FIG. 13A illustrates the state of the subsurface vasculature when measurement device 1300 is inactive. The state of the subsurface vasculature when measurement device 1300 is active during a measurement period is illustrated in FIG. 13B. At this time, collection magnet 1370 generates a magnetic field 1232 sufficient to cause functionalized magnetic particles 1340 present in a lumen of the subsurface vasculature 1330 to collection in a region proximal to the magnet 1370. Signal source 1360 transmits an interrogating signal 1362 into the portion of subsurface vasculature and detector 1350 is receiving a response signal 1352 generated in response to the interrogating signal 1262. The response signal 1352 is related to the binding of a clinically relevant analyte present in the subsurface vasculature to the functionalized magnetic particles 1340. As described above, in some embodiments, an interrogating signal may not be necessary to generate a response signal related to the binding of an analyte to the functionalized magnetic particles.

Both FIGS. 12B and 13B illustrate the path of the interrogating signal (1262, 1362) transmitted by the signal source (1260, 1360) and the responsive signal (1252, 1352) detected by the detector (1250, 1350) essentially overlapping over a portion of subsurface vasculature. In some examples, the signal source (1260, 1360) and the detector (1250, 1350) may be angled towards each other so that they are interrogating and detecting from essentially the same area of subsurface vasculature. However, in some instances, such as in the example shown in FIG. 11B, the paths of the interrogating signal (1262, 1362) transmitted by the signal source (1260, 1360) and the responsive signal (1252, 1352) detected by the detector (1250, 1350) may not overlap.

VI. ILLUSTRATIVE METHODS FOR REAL-TIME, HIGH-DENSITY PHYSIOLOGICAL DATA COLLECTION USING A WRIST MOUNTED DEVICE

Figure 14:
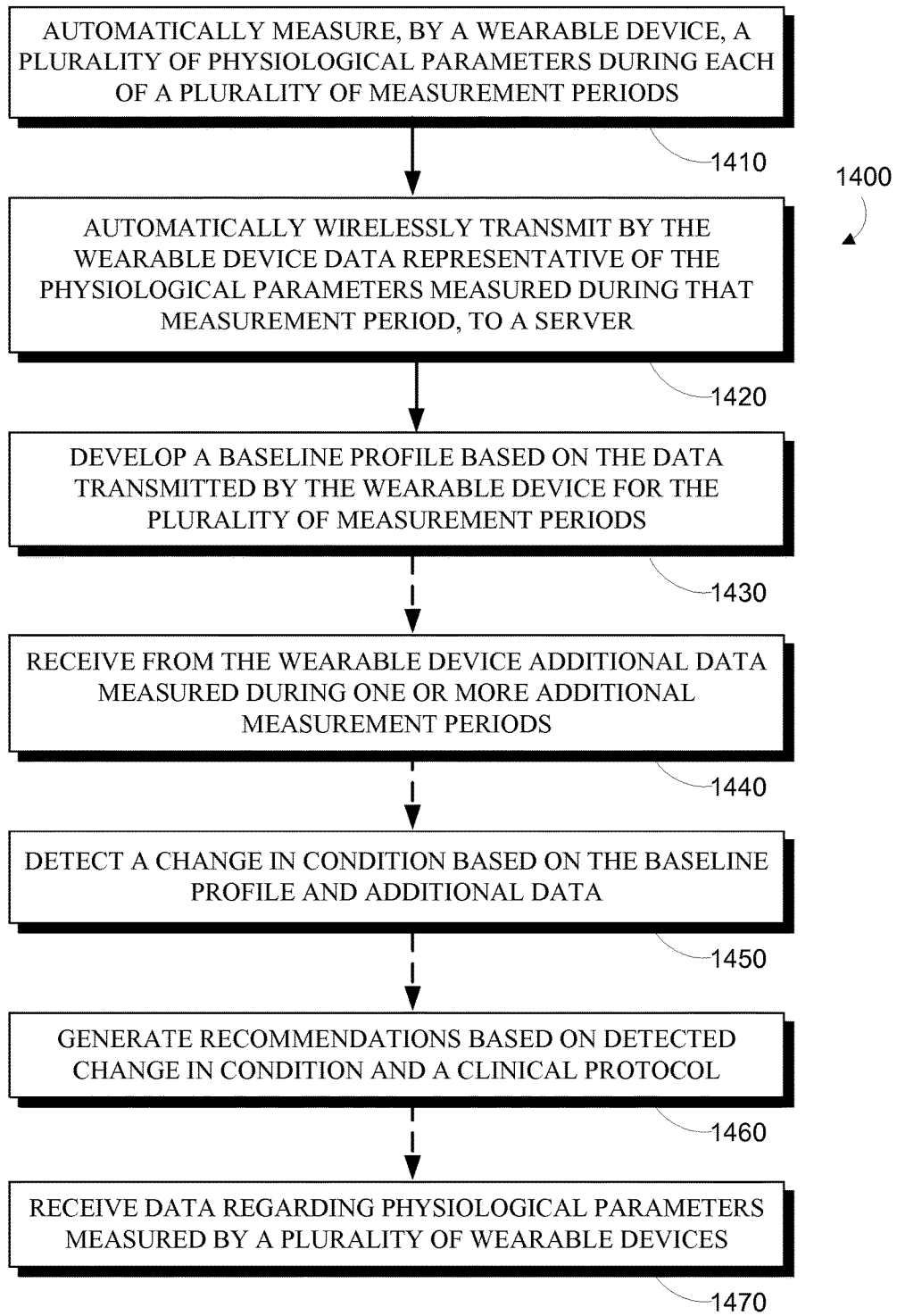
FIG. 14 is a flowchart of an example method for using a wearable device to take real-time, high-density, non-invasive, in vivo measurements of physiological parameters.

FIG. 14 is a flowchart of a method 1400 for using a wearable device to take real-time, high-density, non-invasive, in vivo measurements of physiological parameters. In a first step, the wearable device automatically measures one or more physiological parameters during each of a plurality of measurement periods (1410). The length of the measurement period may be set on the device itself or may be set remotely, for example, by instruction from a remote server. The device may be configured with many measurement periods each day—for example, continuous, every second, every minute, every hour, every 6 hours, etc.—or may be configured to take measurements once a week or once a month. Further, a different measurement period may be set for each of the physiological parameters being measured. The measurement periods may extend through a plurality of consecutive days and each of the consecutive days may include multiple measurement periods. Each of the consecutive days may further include at least twenty-four measurement periods and the plurality of consecutive days may include at least thirty days. At least some of the physiological parameters are measured by non-invasively detecting one or more analytes in blood circulating in subsurface vasculature proximate to the wearable device.

After conclusion of a measurement period, for each of the plurality of measurement periods, the wearable device transmits to a server data representative of the physiological parameters measured during that measurement period (1420). The wearable device may be configured to automatically transmit the data to a server, may be configured to transmit on command of the wearer, or may be configured to transmit on instruction from a remote server. Further, the device may be configured to automatically transmit the data at the end of each measurement period, or at some more frequent or infrequent rate. For example, the device could be configured to transmit every five minutes, at the end of each day, at the end of the month, at nighttime only, etc.

In response, the server is configured to develop a baseline profile based on the data transmitted by the wearable device for the plurality of measurement periods (1430). In some embodiments, the baseline profile includes an individual baseline profile based on the data transmitted by the wearable device for the plurality of measurement periods for an individual user wearing the wearable device. As described above, the baseline profile may include patterns for how one or more of the wearer's physiological parameters typically change over time, such as during the course of a day, a week, or a month. The baseline profile may further include threshold values of certain target analytes, above or below which a medical condition may be indicated.

After the server has developed an individual baseline profile for a wearer of the device, the server may receive additional data regarding the physiological parameters from the wearable device measured during one or more additional measurement periods (1440). The server may then compare the additional data, collected over additional measurement periods, to the individual baseline profile. If the additional data is consistent with the patterns embodied in the individual baseline profile, the server may determine that the wearer's condition has not changed. On the other hand, if the additional data deviates from the patterns embodied in the baseline profile, the server may detect a change in the wearer's condition (1450). The change in condition could, for example, indicate that the wearer has developed a disease, disorder, or other adverse medical condition or may be at risk for a severe medical condition, such as a stroke or a heart attack, in the near future.

If the server detects a change in condition based on the individual baseline profile and the additional data, it may generate one or more recommendations based on the detected change in condition and a clinical protocol (1460). For example, the server may generate a recommendation that the wearer take a particular medication or supplement, schedule an appointment with a medical professional, go to the hospital to seek immediate medical attention, abstain from certain activities, etc. The server may also be configured to receive data regarding physiological parameters measured by a plurality of wearable devices (1470) and use that data to develop, at least in part, the clinical protocol. The clinical protocol may also be developed based, at least in part, on any known health information or medical history of the wearer, and/or on recognized standards of care in the medical field. The wearable device may receive the one or more recommendations generated by the server (1470) and providing an indication of the one or more recommendations via a user interface on the wearable device.

In some embodiments, the server may be configured to receive data regarding physiological parameters measured by a plurality of wearable devices. The server may use this data collected from a plurality of wearable devices—worn by a plurality of users—to develop, at least in part, a population baseline profile. Such population baseline profiles may be used, for example, for comparison with an individual's baseline profile. Those of skill in the art will readily recognize that comparison of an individual's physiological parameters measured over time to that individual's own baseline may not be sufficient to recognize an abnormality in that physiological parameter. For example, while a physiological parameter for an individual wearer of the device may not deviate from that individual's baseline, that individual baseline may be well above the population baseline generated from data collected from a plurality of wearers of the device. Thus, comparison to what is "normal" or "average" for a population may be necessary for effective identification or prevention of a medical condition in an individual.

Accordingly, the server may further be configured to receive from the wearable device additional data measured during one or more additional measurement periods, detect a change in condition based on the population baseline profile and the additional data, and generate one or more recommendations based on the detected change in condition and a clinical protocol. The wearable device may receive the one or more recommendations generated by the server and provide an indication of the one or more recommendations via a user interface on the wearable device.

Figure 15:
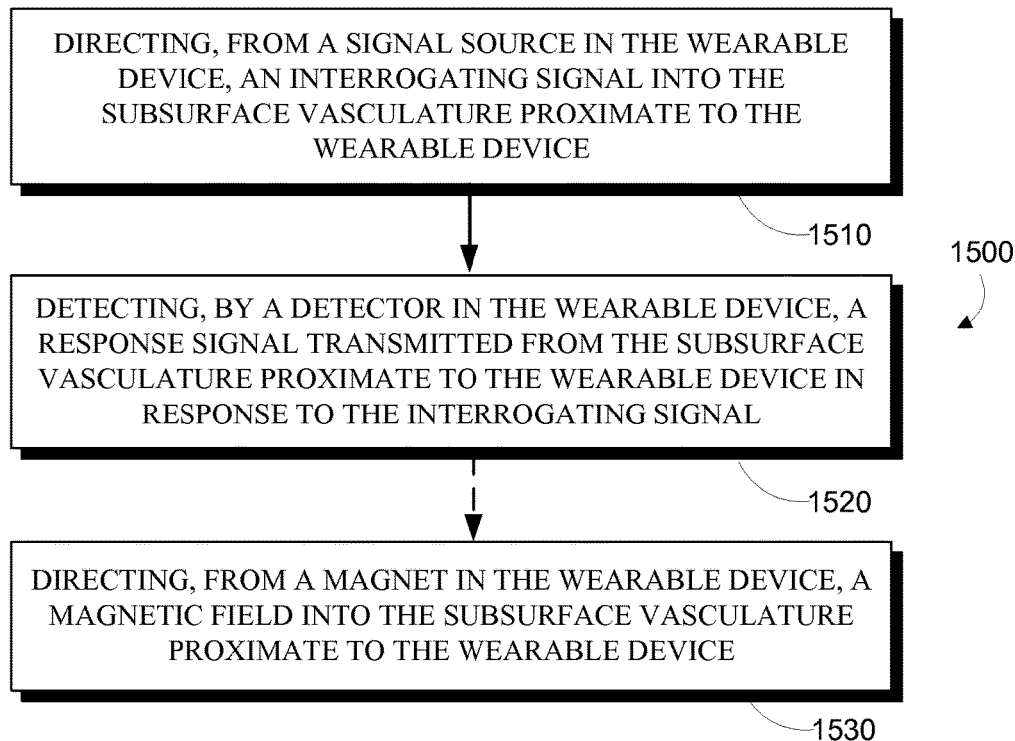
FIG. 15 is a flowchart of an example method for using a wearable device to take real-time, high-density, non-invasive, in vivo measurements of physiological parameters, in particular steps for measuring one or more analytes in blood circulating in subsurface vasculature proximate to the wearable device.

In further embodiments, the method may include introducing functionalized particles into the blood, wherein the functionalized magnetic particles are configured to bind to the one or more analytes. As shown in FIG. 15, the wearable device may non-invasively measure one or more analytes in blood circulating in subsurface vasculature proximate to the wearable device by directing, from a signal source in the wearable device, an interrogating signal into the subsurface vasculature proximate to the wearable device (1510). As discussed above, this step may not be necessary in cases where the functionalized particles generate a response signal related to binding of the one or more analytes without the need for an interrogating signal. In any case, the wearable device may detect, with a detector, a response signal transmitted from the subsurface vasculature proximate to the wearable device in response to the interrogating signal (1520). The response signal is related to binding of the one or more analytes to the functionalized particles. In examples where an interrogating signal is used, the interrogating signal may include a time-varying magnetic field and the response signal may include an externally-detectable physical motion due to the time-varying magnetic field. The interrogating signal may include an electromagnetic pulse (e.g., a radio frequency (RF) pulse) and the response signal may include a magnetic resonance (MR) signal. The interrogating signal may include electromagnetic radiation having a wavelength between about 400 nanometers and about 1600 nanometers, more particularly, a wavelength between about 500 nanometers and about 1000 nanometers. Where the functionalized particles also include a fluorophore, the response signal may include fluorescence radiation transmitted by the fluorophore in response to the interrogating signal.

In some examples, the functionalized particles may also be magnetic. The process of measuring one or more analytes in blood circulating in subsurface vasculature may further include directing, from a magnet in the wearable device, a magnetic field into the subsurface vasculature proximate to the wearable device (1530). The magnetic field is sufficient to cause the functionalized magnetic particles to collect in a lumen of the subsurface vasculature proximate to the wearable device.

Figure 16:
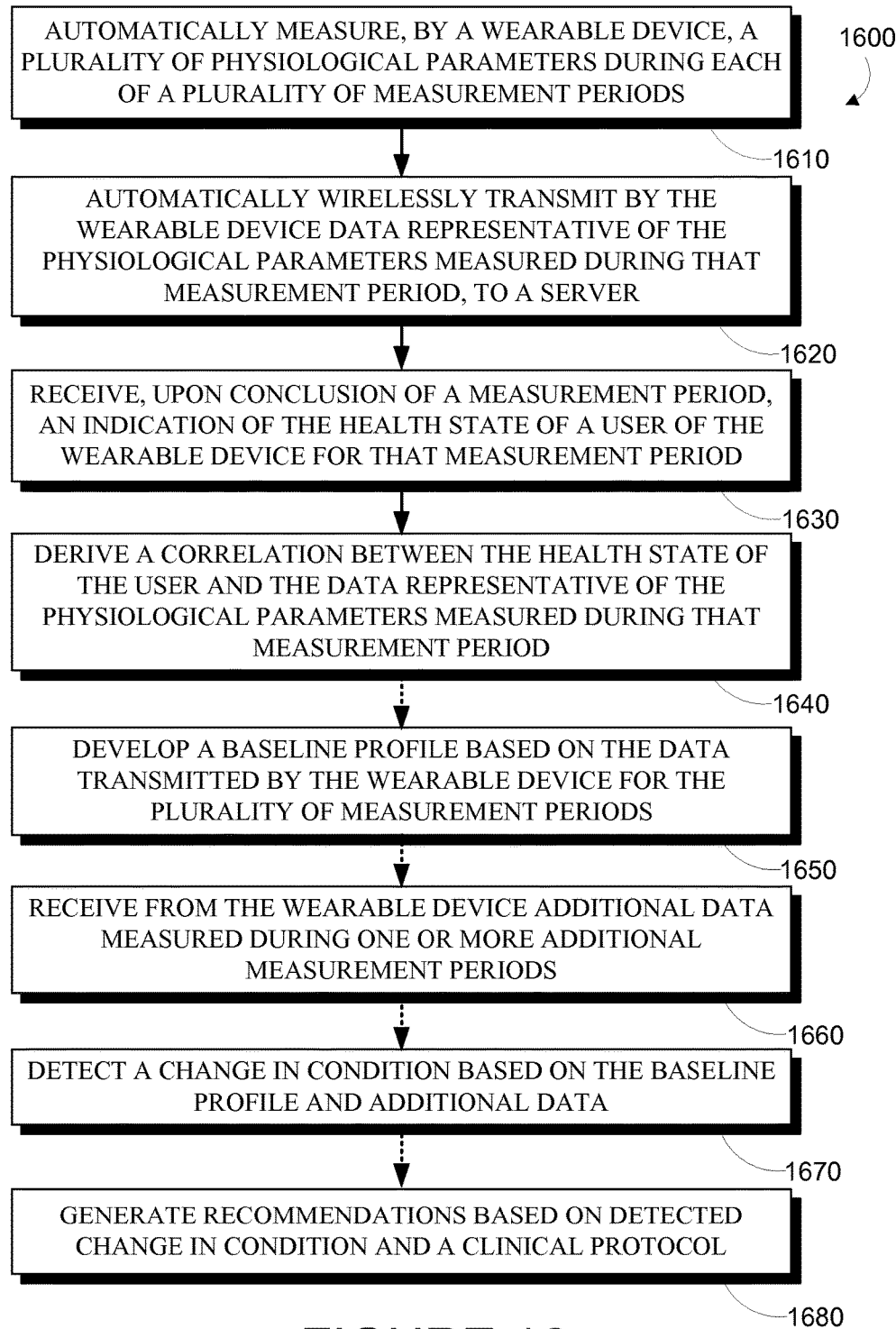
FIG. 16 is a flowchart of an example method for using a wearable device to take real-time, high-density, non-invasive, in vivo measurements of physiological parameters.

FIG. 16 is a flowchart of a method 1600 for using a wearable device to take real-time, high-density, non-invasive, in vivo measurements of physiological parameters. In a first step, the wearable device automatically measures one or more physiological parameters during each of a plurality of measurement periods (1610). The measurement periods may extend through a plurality of consecutive days, wherein each of the consecutive days includes multiple measurement periods. At least some of the physiological parameters are measured by non-invasively detecting one or more analytes in blood circulating in subsurface vasculature proximate to the wearable device.

Upon conclusion of a measurement period for each of the plurality of measurement periods, the wearable device automatically wirelessly transmits to a server data representative of the physiological parameters measured during that measurement period (1620). The server may be configured to receive, upon conclusion of a measurement period, an indication of the health state of a user of the wearable device for that measurement period and derive a correlation between the health state of the user and the data representative of the physiological parameters measured during that measurement period (1630). For example, the server may be configured to recognize patterns, for example, every time a physiological parameter reaches or drops to a certain level, the wearer of the device indicates that he or she experiences a migraine. Recognition of these patterns or correlations may help medical professionals to recognize, prevent, diagnose and/or treat of health conditions in that individual. Further, the server may be configured to use these correlation to alert the user that a medical condition may be imminent.

A baseline profile may be developed by the server based on the data transmitted by the wearable device for the plurality of measurement periods (1650). The server may further be configured to receive from the wearable device additional data representative of the physiological parameters measured during one or more additional measurement periods (1660), detect a change in condition based on the baseline profile and the additional data (1670), and generate one or more recommendations based on the detected change in condition and a clinical protocol (1680). The clinical protocol may be developed based, at least in part, on the derived correlation. For example, the clinical protocol may indicate that a medical condition may be imminent based on a comparison between current measurement of a physiological parameter and the derived correlation between previously measured physiological parameters and previously reported health state.

In a further example, the server may be configured to receive data regarding physiological parameters measured by a plurality of wearable devices and receive an indication of the health state of the users of the plurality of wearable devices for a plurality of measurement periods. The server may then derive a correlation between the health state of the users and the data representative of the physiological parameters measured during the plurality of measurement periods. Population data of this kind may be significant in that such correlations may never before have been drawn between that physiological parameter and a particular health condition. Such correlations may be used in prediction, prevention, diagnoses and treatment of health conditions. The server may also be configured to receive from the wearable device additional data representative of the physiological parameters measured during one or more additional measurement periods and generate one or more recommendations based on the received additional data and a clinical protocol, wherein the clinical protocol is developed based, at least in part, on the derived correlation.

In a further example, the wearable device itself may be configured to perform the steps described above as being performed by a remote server. For example, the wearable device may be configured to analyze the data representative of the physiological parameters, generate a baseline profile, compare data collected from additional measurement periods to the baseline profile, and generate recommendations based on a clinical protocol. The wearable device may further be configured to transmit, either automatically or on some other frequency, certain data to the remote server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

V. CONCLUSION

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:

1. A method, comprising:
automatically measuring, by a wearable device being worn on an external surface of a body of a user proximate a portion of subsurface vasculature, one or more physiological parameters during each of a plurality of measurement periods, wherein the one or more physiological parameters are measured by:
directing, from a magnet in the wearable device, a magnetic field into the portion of subsurface vasculature, wherein the magnetic field causes functionalized magnetic particles that have been introduced into the body to collect in a lumen of the portion of subsurface vasculature;
directing, from a signal source in the wearable device, an interrogating signal into the portion of subsurface vasculature; and
detecting, by a detector in the wearable device, a response signal transmitted from the portion of subsurface vasculature in response to the interrogating signal, wherein the response signal is indicative of binding of one or more analytes to the functionalized magnetic particles collected in the lumen of the subsurface vasculature by the magnetic field;
using the one or more physiological parameters measured by the wearable device during the plurality of measurement periods to develop a baseline profile of the user, such that the baseline profile of the user includes patterns for how the user's one or more physiological parameters change over time;
measuring, using the magnet, signal source, and detector in the wearable device, the one or more physiological parameters during one or more additional measurement periods to obtain additional data;
detecting a change in condition from a comparison of the baseline profile and the additional data; and
in response to detecting the change in condition, generating one or more recommendations for the user and providing, via a user interface in the wearable device, an indication of the one or more recommendations.

2. The method of claim 1, wherein the indication comprises at least one of a visual component, an auditory component, or a tactile component.

3. The method of claim 1, wherein the one or more recommendations comprise a recommendation that the user take a particular medication.

4. The method of claim 1, wherein the one or more recommendations comprise a recommendation that the user schedule an appointment with a medical professional.

5. The method of claim 1, wherein the one or more recommendations comprise a recommendation that the user seek immediate medical attention.

6. The method of claim 1, wherein the one or more recommendations comprise a recommendation that the user abstain from an activity.

7. The method of claim 1, further comprising:
introducing the functionalized magnetic particles into the body of the user by injection, ingestion, inhalation, or transdermally.

8. A wearable device, comprising:
a magnet;
a signal source;
a detector;
a processor;
a user interface; and
a non-transitory computer-readable medium having stored therein instructions that are executable by the processor to cause the wearable to perform functions comprising:
automatically measuring one or more physiological parameters of a user of the wearable device during each of a plurality of measurement periods, wherein the wearable device is worn on an external body surface of the user proximate a portion of subsurface vasculature, wherein the one or more physiological parameters are measured by:
directing, from the magnet, a magnetic field into the portion of subsurface vasculature, wherein the magnetic field causes functionalized magnetic particles that have been introduced into the body to collect in a lumen of the portion of subsurface vasculature;
directing, from the signal source, an interrogating signal into the portion of subsurface vasculature; and
detecting, by the detector, a response signal transmitted from the portion of subsurface vasculature in response to the interrogating signal, wherein the response signal is indicative of binding of one or more analytes to the functionalized magnetic particles collected in the lumen of the subsurface vasculature by the magnetic field;
using the one or more physiological parameters measured during the plurality of measurement periods to develop a baseline profile of the user, such that the baseline profile of the user includes patterns for how the user's one or more physiological parameters change over time;
measuring, using the magnet, signal source, and detector, the one or more physiological parameters during one or more additional measurement periods to obtain additional data;
detecting a change in condition from a comparison of the baseline profile and the additional data; and
in response to detecting the change in condition, generating one or more recommendations for the user and providing, via the user interface, an indication of the one or more recommendations.

9. The wearable device of claim 8, wherein the indication comprises at least one of a visual component, an auditory component, or a tactile component.

10. The wearable device of claim 8, wherein the one or more recommendations comprise a recommendation that the user take a particular medication.

11. The wearable device of claim 8, wherein the one or more recommendations comprise a recommendation that the user schedule an appointment with a medical professional.

12. The wearable device of claim 8, wherein the one or more recommendations comprise a recommendation that the user seek immediate medical attention.

13. The wearable device of claim 8, wherein the one or more recommendations comprise a recommendation that the user abstain from an activity.

14. The wearable device of claim 8, wherein the magnet is an electromagnet.

15. A non-transitory computer readable medium having stored therein instructions that are executable by a processor in a wearable device to cause the wearable device to perform functions comprising:
automatically measuring, by the wearable device, one or more physiological parameters of a user of the wearable device during each of a plurality of measurement periods, wherein the wearable device is worn on an external body surface of the user proximate a portion of subsurface vasculature, wherein the one or more physiological parameters are measured by:
directing, from a magnet in the wearable device, a magnetic field into the portion of subsurface vasculature, wherein the magnetic field causes functionalized magnetic particles that have been introduced into the body to collect in a lumen of the portion of subsurface vasculature;
directing, from a signal source in the wearable device, an interrogating signal into the portion of subsurface vasculature; and
detecting, by a detector in the wearable device, a response signal transmitted from the portion of subsurface vasculature in response to the interrogating signal, wherein the response signal is indicative of binding of one or more analytes to the functionalized magnetic particles collected in the lumen of the subsurface vasculature by the magnetic field;
using the one or more physiological parameters measured by the wearable device during the plurality of measurement periods to develop a baseline profile of the user, such that the baseline profile of the user includes patterns for how the user's one or more physiological parameters change over time;
measuring, using the magnet, signal source, and detector in the wearable device, the one or more physiological parameters during one or more additional measurement periods to obtain additional data;
detecting a change in condition from a comparison of the baseline profile and the additional data; and
in response to detecting the change in condition, generating one or more recommendations for the user and providing, via a user interface in the wearable device, an indication of the one or more recommendations.

16. The non-transitory computer readable medium of claim 15, wherein the indication comprises at least one of a visual component, an auditory component, or a tactile component.

17. The non-transitory computer readable medium of claim 15, wherein the one or more recommendations comprise a recommendation that the user take a particular medication.

18. The non-transitory computer readable medium of claim 15, wherein the one or more recommendations comprise a recommendation that the user schedule an appointment with a medical professional.

19. The non-transitory computer readable medium of claim 15, wherein the one or more recommendations comprise a recommendation that the user seek immediate medical attention.

20. The non-transitory computer readable medium of claim 15, wherein the one or more recommendations comprise a recommendation that the user abstain from an activity.

* * * * *